US006863653B1

(12) United States Patent
Zanelli et al.

(10) Patent No.: US 6,863,653 B1

(45) Date of Patent: Mar. 8, 2005

(54) ULTRASOUND DEVICE FOR AXIAL RANGING

(75) Inventors: Claudio I. Zanelli, Sunnyvale, CA (US); Michael J. Rosinko, San Jose, CA (US); Gregg W. Stone, Bethesda, MD (US); Steven A. Daniel, Fremont, CA (US)

(73) Assignee: Eclipse Surgical Technologies, Inc.

(*) Notice: Subject to any disclaimer, the term of this patent is extended or adjusted under 35 U.S.C. 154(b) by 0 days.

(21) Appl. No.: 09/169,747

(22) Filed: Oct. 9, 1998

Related U.S. Application Data

(63) Continuation-in-part of application No. 08/852,977, filed on May 7, 1997.

(51) Int. Cl.[7] .................................... A61B 8/00

(52) U.S. Cl. .................................... 600/437; 600/466

(58) Field of Search .................................... 600/439, 463, 600/466, 467, 471, 437; 606/1, 7, 11

(56) References Cited

U.S. PATENT DOCUMENTS 4,528,652 A 7/1985 Horner et al. .............. 367/162
4,576,177 A 3/1986 Webster, Jr. ................ 128/660
4,658,817 A 4/1987 Hardy ..................... 128/303.1
4,658,827 A 4/1987 He et al. .................... 128/660
4,672,963 A 6/1987 Barken .................... 128/303.1
4,936,281 A 6/1990 Stasz ..................... 128/660.03
5,029,588 A * 7/1991 Yock et al. ................. 600/466
5,109,830 A 5/1992 Cho ............................. 128/4
5,109,859 A 5/1992 Jenkins .................. 128/662.03
5,158,085 A 10/1992 Belikan et al. ........ 128/660.03
5,196,006 A 3/1993 Klopotek et al. ............. 606/12
5,313,950 A 5/1994 Ishikawa et al. ....... 128/662.06
5,350,377 A 9/1994 Winston et al. ............... 606/15
5,377,682 A 1/1995 Ueno et al. .............. 128/660.1
5,380,316 A 1/1995 Aita et al. ..................... 606/7
5,409,000 A 4/1995 Imran ......................... 128/642
5,544,656 A 8/1996 Pitsillides et al. ..... 128/661.04
5,588,432 A * 12/1996 Crowley ..................... 600/439
5,662,124 A 9/1997 Wilk .......................... 128/898
5,713,363 A * 2/1998 Seward et al. .............. 600/466
5,724,975 A 3/1998 Negus et al. .......... 128/661.09
5,853,368 A * 12/1998 Solomon et al. ............ 600/439
5,876,373 A 3/1999 Giba et al. ..................... 604/95
5,893,848 A 4/1999 Negus et al. ................. 606/41
6,001,091 A 12/1999 Murphy-Chutorian et al. . 606/1
6,024,703 A 2/2000 Zanelli et al. ............. 600/437

FOREIGN PATENT DOCUMENTS

DE 195 37 084 A1 4/1997
DE 196 06 610 A1 8/1997
WO WO 97/25101 7/1997
WO WO 98/17185 4/1998
WO WO 98/30144 7/1998
WO WO 98/38916 9/1998

OTHER PUBLICATIONS

Houghten, Richard A.,et al., "Reduction of Sulfoxides in Peptides and Proteins," Methods in Enzymology, vol. 91, pp. 549–559.

(List continued on next page.)

*Primary Examiner*—Marvin M. Lateef
*Assistant Examiner*—Maulin Patel
(74) *Attorney, Agent, or Firm*—Gibson, Dunn & Crutcher, LLP

(57) ABSTRACT

An apparatus for treatment of body tissue includes a treatment apparatus configured to be inserted into a patient. The treatment apparatus has a distal portion, a distal end, a proximal portion and an axis. An ultrasound transducer is positioned at the distal portion of the treatment apparatus. The ultrasound transducer includes a distal ultrasound energy delivery surface and a proximal ultrasound energy delivery surface. An ultrasound energy attenuator member is positioned adjacent to the proximal ultrasound energy delivery surface and is made of a material to at least partially attenuate ultrasound energy from the proximal ultrasound energy delivery surface.

115 Claims, 10 Drawing Sheets

OTHER PUBLICATIONS

Gospodarowicz, Denis et al., "Bovine Brain and Pituitary Fibroblast Growth Factors: Comparison of Their Abilities to Support the Proliferation of Human and Bovine Vascular Endothelial Cells," J. Cell. Biol., vol. 97, pp. 1677–1685, 1983.

Okayama, Hiroto et al., "High Efficiency Cloning of Full-Length cDNA," Molecular and Cellular Biology, vol. 2, No. 2, pp. 161–170, 1982.

Helfman, David M. et al., "Identification of clones that encode chicken tropomyosin by direct immunological screening of a cDNA expression library," Proc. Natl. Acad. Sci. USA, vol. 80, pp. 31–35, Jan. 1983.

Wong, G., et al., "Human GM–CSF: Molecular Cloning of the Complementary DNA and Purification of the Natural and Recombinant Proteins," Science, vol. 228, pp. 810–815, May 17, 1985.

Kirschmeier, Paul T., et al., "Construction and Characterization of a Retroviral Vector Demonstrating Efficient Expression of Cloned cDNA Sequences," DNA, vol. 7, No. 3, pp. 219–225, 1988.

Vieira, Jeffrey et al., "The pUC plasmids, an MI3mp7–derived system for insertion mutagenesis and sequencing with synthetic universal primers," Gene, vol. 19, pp. 259–268, 1982.

Hochuli, E., et al., "New Metal Chelate Adsorbent Selective for Proteins and Peptides Containing Neighbouring Histidine Residues," Journal of Chromatography, vol. 411, pp. 177–184, 1987.

Mulligan, Richard C., et al., "Synthesis of rabiit B–Globin in cultured monkey kidney cells following infection with a SV40 B–globin recombinant genome," Nature, vol. 277, pp. 108–114, Jan. 11, 1979.

* cited by examiner

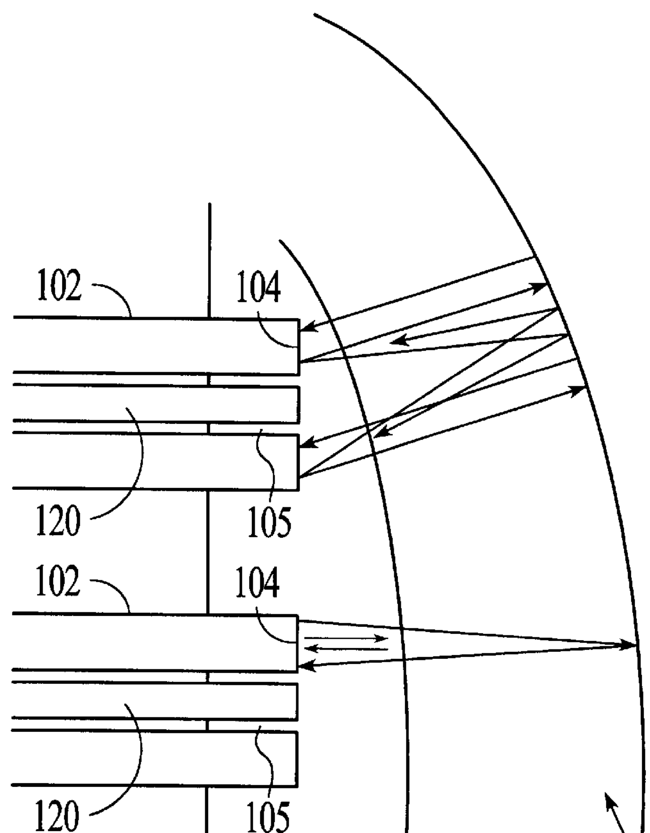
FIG. 10A
FIG. 10B
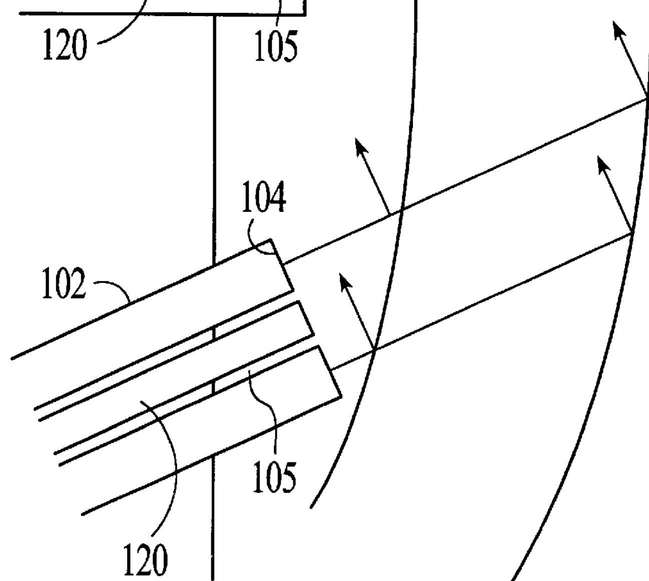
FIG. 10C
FIG. 10

```
                              SEQUENCE LISTING

<160> NUMBER OF SEQ ID NOS: 14

<210> SEQ ID NO 1
<211> LENGTH: 641
<212> TYPE: DNA
<213> ORGANISM: Homo sapiens
<220> FEATURE:
<221> NAME/KEY: CDS
<222> LOCATION: (3)..(638)

<400> SEQUENCE: 1

cc cgc ctg ctg ccc aac ctc act ctg tgc tta cag ctg ctg att ctc          47
   Arg Leu Leu Pro Asn Leu Thr Leu Cys Leu Gln Leu Leu Ile Leu
   1               5                   10                  15

tgc tgt caa act cag ggg gag aat cac ccg tct cct aat ttt aac cag         95
Cys Cys Gln Thr Gln Gly Glu Asn His Pro Ser Pro Asn Phe Asn Gln
                20                  25                  30

tac gtg agg gac cag ggc gcc atg acc gac cag ctg agc agg cgg cag        143
Tyr Val Arg Asp Gln Gly Ala Met Thr Asp Gln Leu Ser Arg Arg Gln
            35                  40                  45

atc cgc gag tac caa ctc tac agc agg acc agt ggc aag cac gtg cag        191
Ile Arg Glu Tyr Gln Leu Tyr Ser Arg Thr Ser Gly Lys His Val Gln
        50                  55                  60

gtc ccc ggg cgt cgc atc tcc gcc acc gcc gag gac ggc aac aag ttt        239
Val Pro Gly Arg Arg Ile Ser Ala Thr Ala Glu Asp Gly Asn Lys Phe
    65                  70                  75

gcc aag ctc ata gtg gag acg gac acg ttt ggc agc cgg gtt cgc atc        287
Ala Lys Leu Ile Val Glu Thr Asp Thr Phe Gly Ser Arg Val Arg Ile
80                  85                  90                  95

aaa ggg gct gag agt gag aag tac atc tgt atg aac aag agg ggc aag        335
Lys Gly Ala Glu Ser Glu Lys Tyr Ile Cys Met Asn Lys Arg Gly Lys
                100                 105                 110

ctc atc ggg aag ccc agc ggg aag agc aaa gac tgc gtg ttc acg gag        383
Leu Ile Gly Lys Pro Ser Gly Lys Ser Lys Asp Cys Val Phe Thr Glu
            115                 120                 125

atc gtg ctg gag aac aac tat acg gcc ttc cag aac gcc cgg cac gag        431
Ile Val Leu Glu Asn Asn Tyr Thr Ala Phe Gln Asn Ala Arg His Glu
        130                 135                 140

ggc tgg ttc atg gtc ttc acg cgg cag ggg cgg ccc cgc cag gct tcc        479
Gly Trp Phe Met Val Phe Thr Arg Gln Gly Arg Pro Arg Gln Ala Ser
    145                 150                 155
```

-continued

```
cgc agc cgc cag aac cag cgc gag gcc cac ttc atc aag cgc ctc tac      527
Arg Ser Arg Gln Asn Gln Arg Glu Ala His Phe Ile Lys Arg Leu Tyr
160                 165                 170                 175

caa ggc cag ctg ccc ttc ccc aac cac gcc gag aag cag aag cag ttc      575
Gln Gly Gln Leu Pro Phe Pro Asn His Ala Glu Lys Gln Lys Gln Phe
                180                 185                 190

gag ttt gtg ggc tcc gcc ccc acc cgt cgg acc aag cgc aca cgg cgg      623
Glu Phe Val Gly Ser Ala Pro Thr Arg Arg Thr Lys Arg Thr Arg Arg
            195                 200                 205

ccc cag ccc ctc acg tag                                              641
Pro Gln Pro Leu Thr
        210
```

<210> SEQ ID NO 2
<211> LENGTH: 212
<212> TYPE: PRT
<213> ORGANISM: Homo sapiens

<400> SEQUENCE: 2

```
Arg Leu Leu Pro Asn Leu Thr Leu Cys Leu Gln Leu Leu Ile Leu Cys
1               5                   10                  15

Cys Gln Thr Gln Gly Glu Asn His Pro Ser Pro Asn Phe Asn Gln Tyr
            20                  25                  30

Val Arg Asp Gln Gly Ala Met Thr Asp Gln Leu Ser Arg Arg Gln Ile
        35                  40                  45

Arg Glu Tyr Gln Leu Tyr Ser Arg Thr Ser Gly Lys His Val Gln Val
    50                  55                  60

Pro Gly Arg Arg Ile Ser Ala Thr Ala Glu Asp Gly Asn Lys Phe Ala
65                  70                  75                  80

Lys Leu Ile Val Glu Thr Asp Thr Phe Gly Ser Arg Val Arg Ile Lys
                85                  90                  95

Gly Ala Glu Ser Glu Lys Tyr Ile Cys Met Asn Lys Arg Gly Lys Leu
            100                 105                 110

Ile Gly Lys Pro Ser Gly Lys Ser Lys Asp Cys Val Phe Thr Glu Ile
        115                 120                 125

Val Leu Glu Asn Asn Tyr Thr Ala Phe Gln Asn Ala Arg His Glu Gly
    130                 135                 140

Trp Phe Met Val Phe Thr Arg Gln Gly Arg Pro Arg Gln Ala Ser Arg
145                 150                 155                 160

Ser Arg Gln Asn Gln Arg Glu Ala His Phe Ile Lys Arg Leu Tyr Gln
                165                 170                 175

Gly Gln Leu Pro Phe Pro Asn His Ala Glu Lys Gln Lys Gln Phe Glu
            180                 185                 190

Phe Val Gly Ser Ala Pro Thr Arg Arg Thr Lys Arg Thr Arg Arg Pro
        195                 200                 205

Gln Pro Leu Thr
    210
```

<210> SEQ ID NO 3
<211> LENGTH: 32
<212> TYPE: DNA
<213> ORGANISM: Artificial Sequence
<220> FEATURE:
<223> OTHER INFORMATION: Synthetic polynucleotide sequence

<400> SEQUENCE: 3

```
gccagaccat ggagaatcac ccgtctccta at                                   32
```

<210> SEQ ID NO 4
<211> LENGTH: 30
<212> TYPE: DNA
<213> ORGANISM: Artificial Sequence
<220> FEATURE:
<223> OTHER INFORMATION: Synthetic polynucleotide sequence

<400> SEQUENCE: 4
gatttaagat ctcgtgaggg gctggggccg 30

<210> SEQ ID NO 5
<211> LENGTH: 30
<212> TYPE: DNA
<213> ORGANISM: Artificial Sequence
<220> FEATURE:
<223> OTHER INFORMATION: Synthetic polynucleotide sequence

<400> SEQUENCE: 5
ctagtggatc ccgagaatca cccgtctcct 30

<210> SEQ ID NO 6
<211> LENGTH: 30
<212> TYPE: DNA
<213> ORGANISM: Artificial Sequence
<220> FEATURE:
<223> OTHER INFORMATION: Synthetic polynucleotide sequence

<400> SEQUENCE: 6
cgacttctag aacctcgggg atctggctcc 30

<210> SEQ ID NO 7
<211> LENGTH: 17
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (6)..(11)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa can be any naturally occurring amino acid

<400> SEQUENCE: 7

Gly Xaa Leu Xaa Ser Xaa Xaa Xaa Xaa Xaa Xaa Asp Cys Xaa Phe Xaa
1 5 10 15

Glu

<210> SEQ ID NO 8
<211> LENGTH: 17
<212> TYPE: PRT
<213> ORGANISM: Artificial Sequence
<220> FEATURE:
<223> OTHER INFORMATION: Synthetic peptide
<220> FEATURE:

-continued

<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (6)..(11)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa can be any naturally occurring amino acid

<400> SEQUENCE: 8

```
Gly Xaa Leu Xaa Thr Xaa Xaa Xaa Xaa Xaa Xaa Asp Cys Xaa Phe Xaa
1               5                   10                  15

Glu
```

<210> SEQ ID NO 9
<211> LENGTH: 17
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (6)..(11)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa can be any naturally occurring amino acid

<400> SEQUENCE: 9

```
Gly Xaa Leu Xaa Ala Xaa Xaa Xaa Xaa Xaa Xaa Asp Cys Xaa Phe Xaa
1               5                   10                  15

Glu
```

<210> SEQ ID NO 10
<211> LENGTH: 17
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature -continued

```
<222> LOCATION: (6)..(11)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa can be any naturally occurring amino acid

<400> SEQUENCE: 10

Gly Xaa Leu Xaa Gly Xaa Xaa Xaa Xaa Xaa Xaa Asp Cys Xaa Phe Xaa
1               5                   10                  15

Glu


<210> SEQ ID NO 11
<211> LENGTH: 17
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (6)..(11)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa can be any naturally occurring amino acid

<400> SEQUENCE: 11

Gly Xaa Leu Xaa Ser Xaa Xaa Xaa Xaa Xaa Xaa Glu Cys Xaa Phe Xaa
1               5                   10                  15

Glu


<210> SEQ ID NO 12
<211> LENGTH: 17
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (6)..(11)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: misc_feature
<222> LOCATION: (16)..(16)
```

-continued

<223> OTHER INFORMATION: Xaa can be any naturally occurring amino acid

<400> SEQUENCE: 12

```
Gly Xaa Leu Xaa Thr Xaa Xaa Xaa Xaa Xaa Xaa Glu Cys Xaa Phe Xaa
1               5                   10                  15

Glu
```

<210> SEQ ID NO 13
<211> LENGTH: 17
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (6)..(11)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa can be any naturally occurring amino acid

<400> SEQUENCE: 13

```
Gly Xaa Leu Xaa Ala Xaa Xaa Xaa Xaa Xaa Xaa Glu Cys Xaa Phe Xaa
1               5                   10                  15

Glu
```

<210> SEQ ID NO 14
<211> LENGTH: 17
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (6)..(11)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa can be any naturally occurring amino acid

<400> SEQUENCE: 14

```
Gly Xaa Leu Xaa Gly Xaa Xaa Xaa Xaa Xaa Xaa Glu Cys Xaa Phe Xaa
1               5                   10                  15

Glu
```

ULTRASOUND DEVICE FOR AXIAL RANGING

CROSS-REFERENCE TO RELATED APPLICATIONS

This application is a continuation-in-part of U.S. patent application Ser. No. 08/852,977 filed May 7, 1997, entitled "ULTRASOUND DEVICE FOR AXIAL RANGING", incorporated herein by reference

BACKGROUND OF THE INVENTION

1. Field of the Invention

The present invention relates generally to catheters, MIS or other surgical apparatus for therapeutic applications. More particularly, the invention relates to a catheter, MIS or other elongated body including an ultrasound transducer that makes it particularly suited for determining the depth of dynamic tissue in beating heart laser-assisted transmyocardial revascularization (TMR), but not limited to such application. As the ultrasound transducer is fired, an acoustic wave is generated and a signal is reflected back to the transducer from anatomical structures, thus providing information on the position of the catheter, MIS or other surgical apparatus in relation to the anatomical structure.

2. Description of Related Art

Transmyocardial Revascularization

In the treatment of heart disease, one method of improving myocardial blood supply is called transmyocardial revascularization (TMR), the creation of channels in the myocardium of the heart. The procedure using needles in a form of surgical Amyocardial acupuncture has been used clinically since the 1960s. Deckelbaum. L. I., Cardiovascular Applications of Laser Technology, Lasers in Surgery and Medicine 15:315–341 (1994). The technique relieves ischemia by allowing blood to pass from the ventricle through the channels either directly into other vessels communicating with the channels or into myocardial sinusoids which connect to the myocardial microcirculation.

Numerous surgical TMR studies have been performed, including early studies using needles to perform myocardial acupuncture, or boring, to mechanically displace and/or remove tissue. Such studies have involved surgically exposing the heart and sequentially inserting needles to form a number of channels through the epicardium, myocardium, and endocardium to allow blood from the ventricle to perfuse the channels. The early studies using needles showed that the newly created channels were subject to acute thrombosis followed by organization and fibrosis of clots resulting in channel closure. Interest in TMR using needles waned with the knowledge that such channels did not remain open. However, interest in TMR procedures recurred with the advent of medical lasers used to create TMR channels. Histological evidence of patent, endothelium-lined tracts within laser-created channels shows that the lumen of laser channels can become hemocompatible and resists occlusion. Additionally, recent histological evidence shows probable new vessel formation adjacent collagen occluded transmyocardial channels, thereby suggesting benefits from TMR with or without the formation of channels which remain patent.

Surgical TMR procedures using laser energy have been described in the prior art. U.S. Pat. No. 4,658,817 issued Apr. 21, 1987 to Hardy teaches a method and apparatus for surgical TMR using a $CO_2$ laser connected to an articulated arm having a handpiece attached thereto. The handpiece emits laser energy from a single aperture and is moved around the epicardial surface of the heart to create the desired number of channels. U.S. Pat. No. 5,380,316 issued Jan. 10, 1995 to Aita et al. purports to teach the use of a flexible lasing apparatus which is inserted into the open chest cavity in a surgical procedure. A lens at the distal end of the flexible apparatus is used to focus laser energy, and the apparatus is moved about the epicardial surface of the heart to create the desired number of channels.

Since TMR involves creating channels through the endocardium into the lower left chamber of the heart, it is also desirable to create TMR channels percutaneously, i.e., by extending a catheter through the vasculature into the ventricle and creating the channels through endocardial surfaces and into myocardium. Performing such percutaneous TMR is desirable for a number of reasons. Percutaneous catheter procedures are typically less traumatic to the patient compared to surgical procedures. Adhesions between the pericardial sac and epicardium are eliminated. Percutaneous TMR with a catheter also offers an alternative solution to persons who are not candidates for surgical procedures.

TMR procedures generally involve creating a plurality of channels within the myocardium. In performing the procedure, particularly percutaneously, it is desirable to have information relating to the depth of channels created, placement of the channels relative to the heart walls and wall thickness of the beating heart. None of the TMR or atherosclerosis devices described above or elsewhere provide such information.

Ultrasound

Ultrasound systems are widely used in medical applications. Sound waves above the frequency normally detectable by the human ear, that is, about 16 to 20 kHz are referred to as ultrasonic waves.

U.S. Pat. No. 4,576,177 issued Mar. 18, 1986 to Webster, Jr. teaches a catheter for removing arteriosclerotic plaque. The apparatus comprises a catheter having an optical fiber for transmitting laser energy and an ultrasound transducer. One embodiment of the device is operated in two different modes—a pulse-echo mode and a pulsed-Doppler mode. In the pulse-echo mode an electrical impulse delivered to the transducer transmits an ultrasound pulse, returning echoes thereof causing electrical signature signals. In the pulsed-Doppler mode, ultrasonic echoes from tone bursts generated in response to electrical bursts transmitted to the ultrasound transducer are used to determine the blood flow velocity at two selected distances from the catheter tip. The tissue signature and the change in blood flow velocity are used to determine the presence of occlusions in blood vessels.

U.S. Pat. No. 4,658,827 issued Apr. 21, 1987 to He et al teaches an ultrasound scanner for tissue characterization. A method and system are disclosed for simultaneously obtaining accurate estimates of the attenuation coefficient of the tissue and an index describing the heterogeneity of the scatterers within the tissue. According to the invention, there is provided a method and apparatus for tissue characterization by transmitting ultrasound energy into the sample tissue, and receiving and processing return echo signals.

U.S. Pat. No. 4,672,963 issued Jun. 16, 1987 to Barken teaches an apparatus and method for computer controlled laser surgery using an ultrasound imaging system.. The position of the laser energy delivery device is monitored with an ultrasound probe. The probe, in conjunction with a computer system, provides a multiplicity of cross-section images of the portion of body tissue within the range of emitted destructive radiation.

U.S. Pat. No. 5,109,859 issued May 5, 1992 to Jenkins teaches an ultrasound guided laser angioplasty system. This system is also directed to the removal of atherosclerotic plaque from coronary arteries of patients with heart disease. A probe with a phased-array ultrasound transducer will produce images of vascular tissue acquired in a plane that is 30° forward of the tip of the catheter to prevent vascular perforation. As above, the catheter provides primarily lateral imaging.

U.S. Pat. No. 5,158,085 issued Oct. 27, 1992 to Belikan et al. teaches a lithotripsy ultrasound locating device using both a locating and a therapy transducer in a fixed relationship. One or more locating ultrasound transducers, each axially rotatable and extendable, generate a signal representing the distance between the locating transducer and the focus of the second transducer, used to transmit therapeutic amounts of ultrasound for fragmentation of a concretion. The locating transducers can have two or more crystal rings, thus having two or more focal ranges, and operate according to annular phased-array principles.

U.S. Pat. No. 5,313,950 issued May 24, 1994 to Ishikawa et al. teaches another ultrasound probe. A rotor moves and/or rotates a transducer and/or a reflector and is driven by a stator outside the object under examination. Both forward as well as lateral firing of ultrasound is taught for obtaining sectional views. However, such rotating mirror technology is distinctly different from the ranging application disclosed herein.

U.S. Pat. No. 5,350,377 issued Sep. 27, 1994 to Winston et al. teaches a medical catheter using optical fibers that transmit both laser energy and ultrasound imaging signals. An external transducer couples to the optical fibers and pulse echoes are received and transmitted back to the transducer along the same optical fibers. Visualization is limited to images as to the configuration, location and character of the tissue in the area of atherosclerotic plaques.

As is evident by a review of the ultrasound imaging prior art, including the foregoing, catheters and other tools for TMR having axial ranging capability, in the sense of determination of the distance from the tip of the firing laser delivery means at a first wall of the heart to a second wall of the heart are virtually unknown. Determination of tissue depth viewed in a forward direction, such as in myocardial tissue for forming TMR channels, would be highly advantageous so as to prevent unwanted perforation of a heart wall and/or to form channels of selected depths.

ADVANTAGES AND SUMMARY OF THE INVENTION

Thus, it is an advantage of the present invention to provide a catheter, MIS or other surgical apparatus and method of use for percutaneous and other surgical procedures, including percutaneous, MIS and surgical TMR, stimulation procedures, agent delivery procedures including but not limited to the delivery of an angiiogensis stimulation agent, which overcome the limitations of the prior art.

It is another advantage of the present invention to provide such an apparatus with an ultrasound guidance system to provide visualization, depth determination, in particular apparatus tip-to-tissue wall distance in tissue for controlled treatment as desired, in particular to prevent perforation of epicardial tissue in percutaneous TMR.

An additional advantage of the present invention allows determination/visualization of the spatial dynamics of the tissue of a beating heart, i.e., one in which the wall depth is constantly changing.

It is a further advantage of the present invention to provide such an apparatus wherein the ultrasound guidance system is small, compact and durable, and either integral with the tip of an elongated body or modular to, interchangeable with and replaceable on an elongated body.

Yet a further advantage of the present invention is to provide such an apparatus for percutaneous, MIS or other surgical placement within a heart chamber, organ aperture or other body opening, the apparatus having at least one central lumen extending along at least part of the length of the tool for guiding a laser delivery means or other functional device to selected surfaces of the heart chamber, organ aperture or other body opening for laser or other treatment thereon, particularly adapted for laser-assisted transmyocardial revascularization (TMR).

One more advantage of the present invention is to provide such ultrasound apparatus with ranging visualization means enabling visualization of piercing of a heart wall, advancement of the piercing tip to a selected depth within myocardium, confirmation of such depth, and controlled, visualized withdrawal of the firing tip during laser activation for TMR.

Another advantage of the present invention is an ultrasound and ECG electrode apparatus that can be used to determine tissue thickness and and changes in thickness during the cardiac cycle. The thickness can be measured during a fixed period of the cardiac cycle or the ultrasound transmission can be synchronized with the ECG signal from the patient.

These and other advantages are obtained in an apparatus for treatment of body tissue that includes a treatment apparatus configured to be inserted into a patient. The treatment apparatus has a distal portion, a distal end, a proximal portion and an axis. An ultrasound transducer is positioned at the distal portion of the treatment apparatus. The ultrasound transducer includes a distal ultrasound energy delivery surface and a proximal ultrasound energy delivery surface. An ultrasound energy attenuator member is positioned adjacent to the proximal ultrasound energy delivery surface and is made of a material to at least partially attenuate ultrasound energy from the proximal ultrasound energy delivery surface.

In another embodiment of the invention, an apparatus for treatment of body tissue includes a treatment apparatus configured to be inserted into a patient. The treatment apparatus includes a distal portion, a distal end, a proximal portion and an axis. An ultrasound transducer is positioned at the distal portion of the treatment apparatus. The ultrasound transducer has a distal ultrasound energy delivery surface and a proximal ultrasound energy delivery surface. An electrode is positioned adjacent to the ultrasound transducer at the treatment apparatus distal end.

In yet another embodiment of the invention, an apparatus for treatment of body tissue includes a treatment apparatus configured to be inserted into a patient. The treatment apparatus has a distal portion, a distal end, a proximal portion, a treatment apparatus lumen and an axis. An ultrasound transducer is positioned at the distal portion of the treatment apparatus. The ultrasound transducer includes a distal ultrasound energy delivery surface and a proximal ultrasound energy delivery surface. A retractable energy delivery device is retractably positioned in the treatment apparatus lumen.

Numerous other advantages and features of the present invention will become readily apparent from the following detailed description of the invention and the embodiments thereof, from the claims and from the accompanying drawings.

BRIEF DESCRIPTION OF THE FIGURES

FIG. 10(*a*) illustrates a determination of wall thickness when the distal tip is in contact with the wall.

FIG. 10(*b*) illustrates the determination of distance between the distal tip of the apparatus and a front boundary surface of a tissue site, as well as the return echo from the back boundary surface of the tissue site.

FIG. 10(*c*) illustrates the return echos from the front and back boundary surfaces of a tissue site are not detected when the angle between the longitudinal axis of the distal tip and the tissue surface falls outside of an acceptance range.

DETAILED DESCRIPTION

Figure 1:
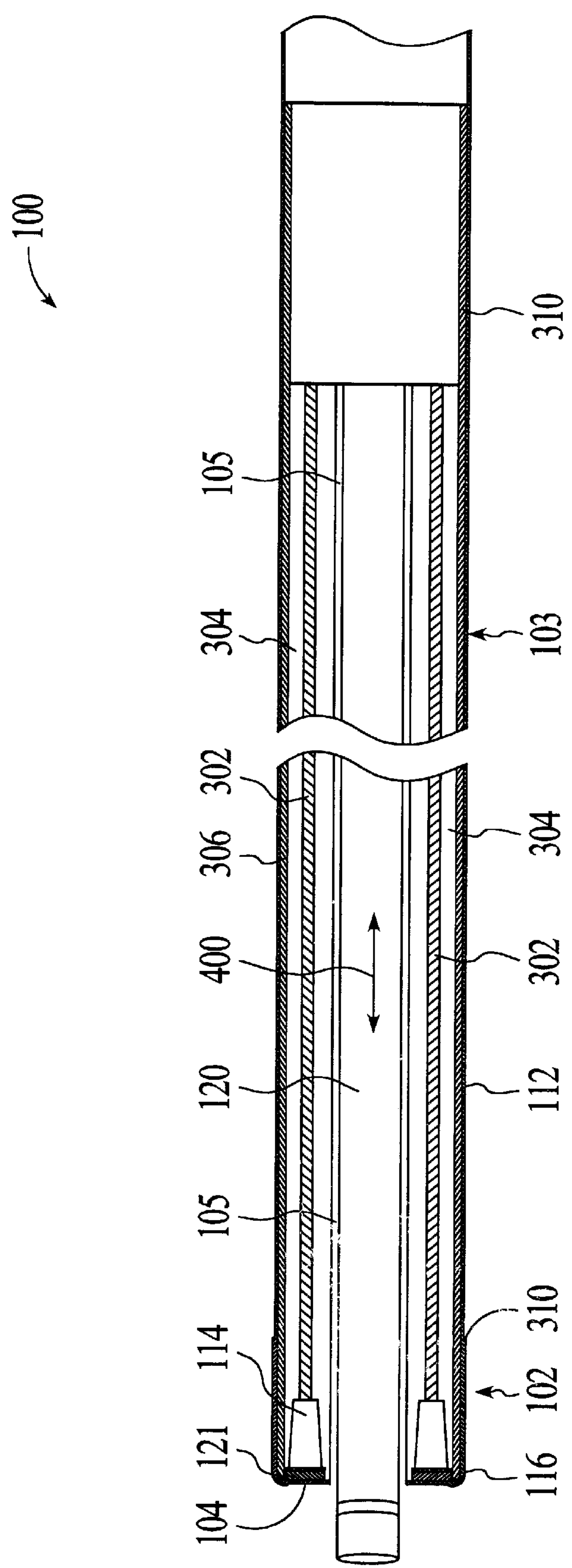
FIG. 1 is a cross section of an embodiment of the disclosed apparatus.

FIG. 1 provides a lateral cross section of an apparatus 100. The apparatus 100 includes a distal tip 102 coupled with an elongated body 103. The distal tip 102 includes an electrode 121 and an ultrasound transducer with a tapered backing 114. The elongated body 103 includes a lumen 105 which extends through the distal tip 102. The lumen 105 can house a laser delivery means 120 which can be translated longitudinally through the lumen as illustrated by the arrow 400. Suitable laser delivery means 120 include, but are not limited to, fiber optics and waveguides.

Figure 2:
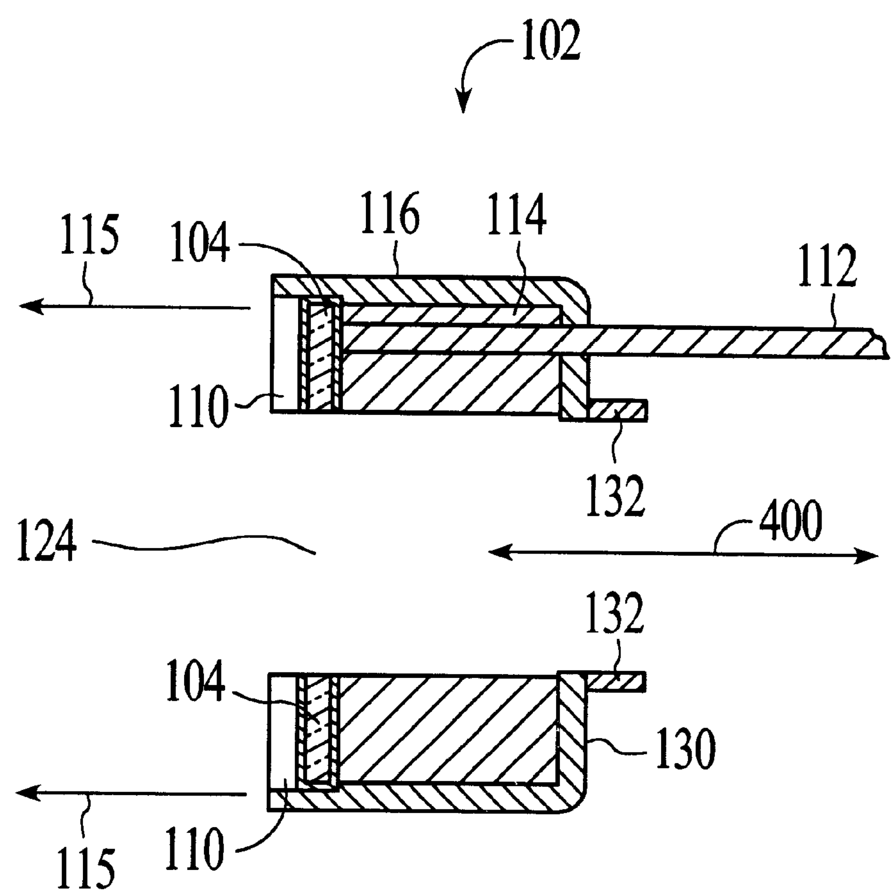
FIG. 2 is a representative section view of a preferred embodiment of a modular distal tip for use with an ultrasound catheter, MIS or other surgical apparatus.

The distal tip 102 can be modular and independent of the elongated body 103 as illustrated in FIG. 2. The distal tip 102 includes a mounting face 130 with a mounting flange 132. The mounting face 130 and mounting flanges 132 provide a means for coupling the distal tip 102 to the distal end of an elongated body 103 such as conventional or other type catheter, MIS or other surgical apparatus. It will be understood by those known in the art that such coupling means includes, and is not limited to, bayonet and other quick connect mounts, screw on or snap on adhesive couplings, etc. Thus, in the preferred embodiment, the distal tip 102 is modular and can be coupled with an elongated body to provide an operable apparatus 100. A suitable elongated body includes, but is not limited to, a conventional catheter, a steerable catheter with a deflectable end portion, an MIS or other surgical apparatus, a modular fiber advance handpiece unit, and other functional devices including fiber advance depth control mechanism, visualization means, drug delivery apparatus, etc.

Although the distal tip 102 is illustrated as being modular in FIGS. 1 and 2, the distal tip 102 can be integral with the elongated body 103.

Figure 3:
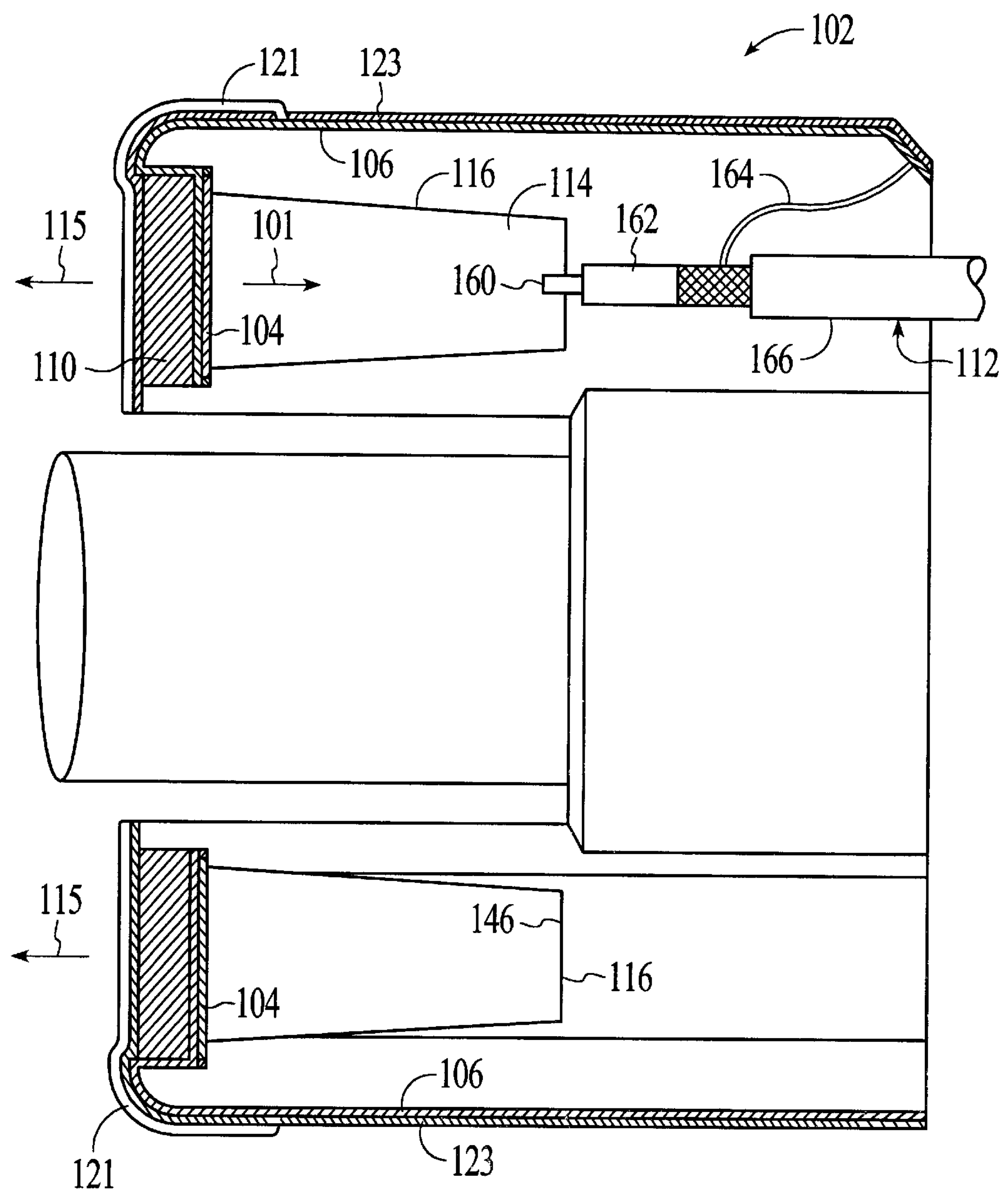
FIG. 3 is a cross section of a distal tip.

FIG. 3 is a cross section of a distal tip. A gold trace 106 or other layer of electrically conductive material covers a distal side the transducer 104 and extends along the sides of the distal tip 102. The gold layer 106 can be applied in any conventional way, preferably by sputtering, vapor deposition, etc. The gold trace forms an electrically conductive layer on the distal side of the transducer 104 and is electrically connected to a coaxial cable 112 which extends through a backing 114. An outer matching layer 110 is positioned adjacent the gold trace 106 and can protect and insulate the gold trace 106. Suitable materials for the matching layer include, but are not limited to, rubber, plastics or composites. The matching layer can be designed to optimize acoustic efficiency by having a thickness of about $\lambda/4$, where $\lambda$ is the wavelength of the ultrasound energy.

The backing 114 can attenuate the ultrasound waves traveling in the direction indicated by the arrow 101. Attenuation can be achieved by constructing the backing from materials as described in U.S. Pat. No. 4,528,652, which is incorporated herein by reference in its entirety. In one embodiment, the backing 114 is made of a material that attenuates sound in the range of 10–30 dB/MHz-cm, preferably in the range of 15–25 dB/MHz-cm and more preferably about 20 dB/MHz-cm. The material for backing 114 is preferably made of at least two materials of different densities and can be a mixture of epoxies and microspheres in proportions selected to provide the ranges in the preceding sentence. A suitable epoxy mixture is EPO-TEK 301, commercially available from Epoxy Technology, Inc., Billerica, Mass. A commercially available microsphere is EXTENDOSPHERES, available from PQ Corporation of Valley Forge, Pa.

At electrically insulating housing 116 in the shape of a cup holds the backing 114. Suitable materials for the housing 116 are preferably soft materials including, but not limited to, polycarbonate, acrylic, PVDF, and the like. The housing 116 provides the backing 114 with a tapered geometric configuration. Tapering increases an echo return path of sound, extends the path of wave travel and provides greater attenuation. Backing 114 substantially eliminates echoes reflected off surface 146 that are larger than −40 dB relative to echoes from a target surface in front of the transducer 104. In one embodiment, the target surface is substantially flat. The backing preferably has a length of 3 mm or less and more preferably 2 mm or less.

The coaxial cable 112 extends through the housing 116. It will be understood that the coaxial cable 112 is but one possible signal interface which couples signals sent to and received from the ultrasound transducer 104 with a signal processing component. The coaxial cable can have a diameter of about 0.0075" as currently available and manufactured by companies such as Temp-Flex Cable, Inc., located in Graften, Mass., to reduce the diameter of the apparatus 100. The coaxial cable 112 is comprised of, from the inside out, a conductor 160, an insulation layer 162, a shielding layer interface 164 and an outer jacket 166. The stripped central conductor 160 is inserted through housing 116 into the backing 114 which is preferably conductive. When the backing is not conductive, the central conductor 160 can extend through the backing and be coupled with the distal side of the transducer 104. The shielding layer interface 164 is coupled with the sputtered metal gold trace 106. The shielding layer interface 164 and the central conductor 160 can be electrically connected to the respective gold trace 106 and backing 114 using simple contact technology, conventional solder, silver or indium epoxy, etc. Applying a voltage across the transducer 104 can actuate the transducer 104 to create an acoustic wave traveling in the direction generally indicated by the arrow 115. Upon reflection of the wave off an anatomical surface, the acoustic echo will return to the transducer 104 and create a signal which can be detected and amplified. It will be understood that the transmitter and receiver combination may be a conventional design and/or may be a single, combined module.

The distal tip 102 can also include an electrode 121. Suitable materials for the electrode 121 include, but are not limited to, gold, platinum and titanium. The electrode 121 has sufficient size to detect electrical currents produced within the body of the patient. Suitable sizes for the electrode include, but are not limited to, 1.0–15 $mm^2$, 1.5–12 $mm^2$ and preferably 5–10 $mm^2$. When it is desirable to increase the size of the electrode 121 to increase sensitivity, the electrode 121 can extend at least partially along the sides of the distal tip 102. The electrode 121 can be a unipolar electrode which would require an external ground reference or a bipolar electrode which could be separated into electrically isolated sections.

The electrode 121 is illustrated as being electrically coupled with the coaxial cable via the gold trace 106 but can be directly coupled with the coaxial cable 112. As a result, electrical signals from the body and from the ultrasound echo travel on the coaxial cable. The electronics for processing the signals from the coaxial cable 112 can include a high pass filter ($f_c$=5 MHz) for the ultrasound echoes and a low pass filter ($f_c$=100 Hz) for the signals from the body.

As will be discussed in more detail below, the electrode 121 can be electrically coupled with a processing unit with logic for processing signals from the electrode 121. These signals can be used at least in part to determine the ECG of the patient. The laser means can also be coupled with the processing unit. As a result, the delivery of laser energy from the laser means can be adjusted in response to the ECG.

An optional coating 123 can cover at least a portion of the distal tip 102. Suitable materials for the coating 123 include, but are not limited to, PARYLENE and TEFLON. The coating can be electrically conductive and cover the electrode or can be electrically insulative and be positioned between the electrode 121 and the matching layer 110 as illustrated in FIG. 3.

It will be understood that the material of construction as well as the shape of the ultrasound transducer 104 can be changed and that a generally flat annulus shaped transducer 104 is but one of many embodiments. Numerous types of ultrasound transducer materials are known, and the class of materials known as piezoelectrics are but one. Likewise, different shaped transducers are known and readily available, the different shapes having different signal propagating and receiving characteristics. As an example but not to limit the scope of the apparatus, the transducer 104 element may have a slightly parabolic shape. Furthermore, a single transducer 104 element can be divided into sections or replaced with a plurality of transducer 104 elements, optionally configured in an array such as a phased array or other. Such configurations comprising more than one transducer 104 element will have associated electrical couplings, drivers, etc.

Figure 4A:
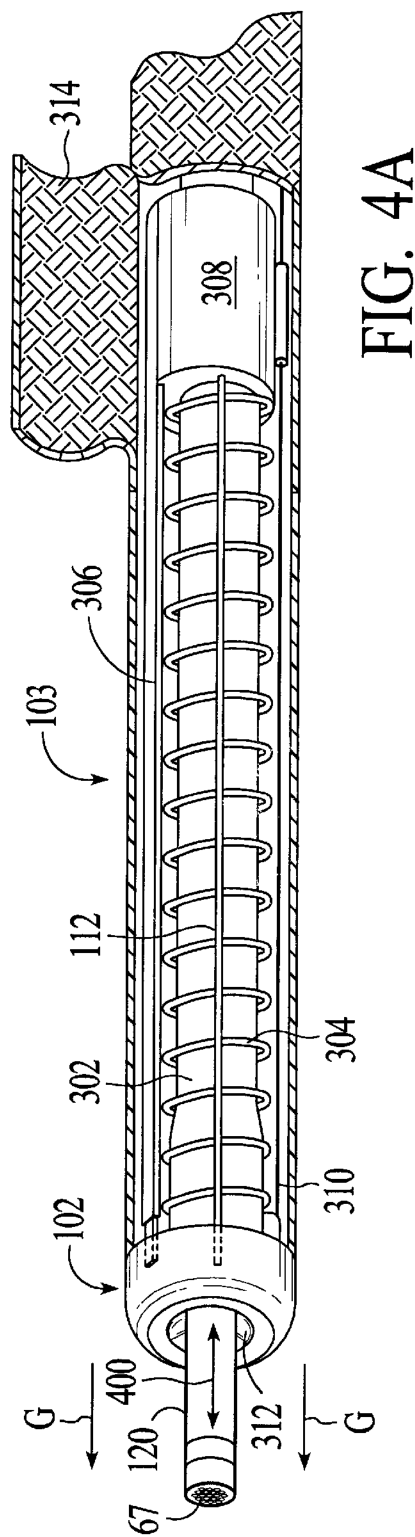
FIGS. 4A and 4B are representative isometric and section views of the distal end and steering means of a preferred embodiment of an ultrasound guidance system.
Figure 4B:
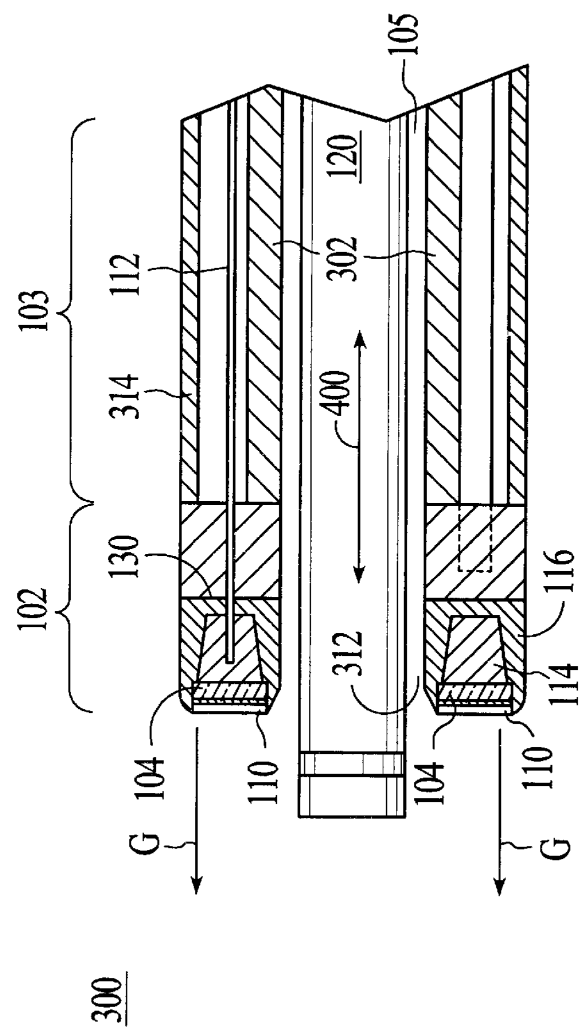

FIGS. 4A and 4B are representative isometric and section views of a steerable apparatus. A central catheter tube 302 is coupled with the mounting face 130 of the distal tip 102. A spiral spring member 304 made of a radiopaque material adds visibility to the bend radius of the apparatus 100 while maintaining steerability of the apparatus 100. A flat planar, rigid shim 306 is coupled between the distal tip 102 and an intermediate sleeve 308. A pull cable 310 also attaches to the distal tip 102 opposite the annular opening 312 through the distal tip 102 so as to act upon the distal tip 102 and cause deflection of the shim 306 as desired to steer the distal tip 102 to selected regions or surfaces. An outer jacket 314 protects the apparatus 100. Embodiments of steerable catheters which can be used with the distal tip are described in U.S. patent application Ser. No. 08/833,352, filed Apr. 3, 1997 and entitled STEERABLE CATHETER, and U.S. patent application Ser. No. 09/156,963 Sep. 18, 1998 entitled "STEERABLE CATHETER WITH TIP ALIGNMENT AND SURFACE CONTACT DETECTION SYSTEM", both of which are incorporated herein by reference.

Additionally, the ultrasound device may be used with curved or pre-bent catheters for delivery of a single optical fiber with or without a lens device for operatively, selectively and/or controllably directing laser energy.

Figure 5:
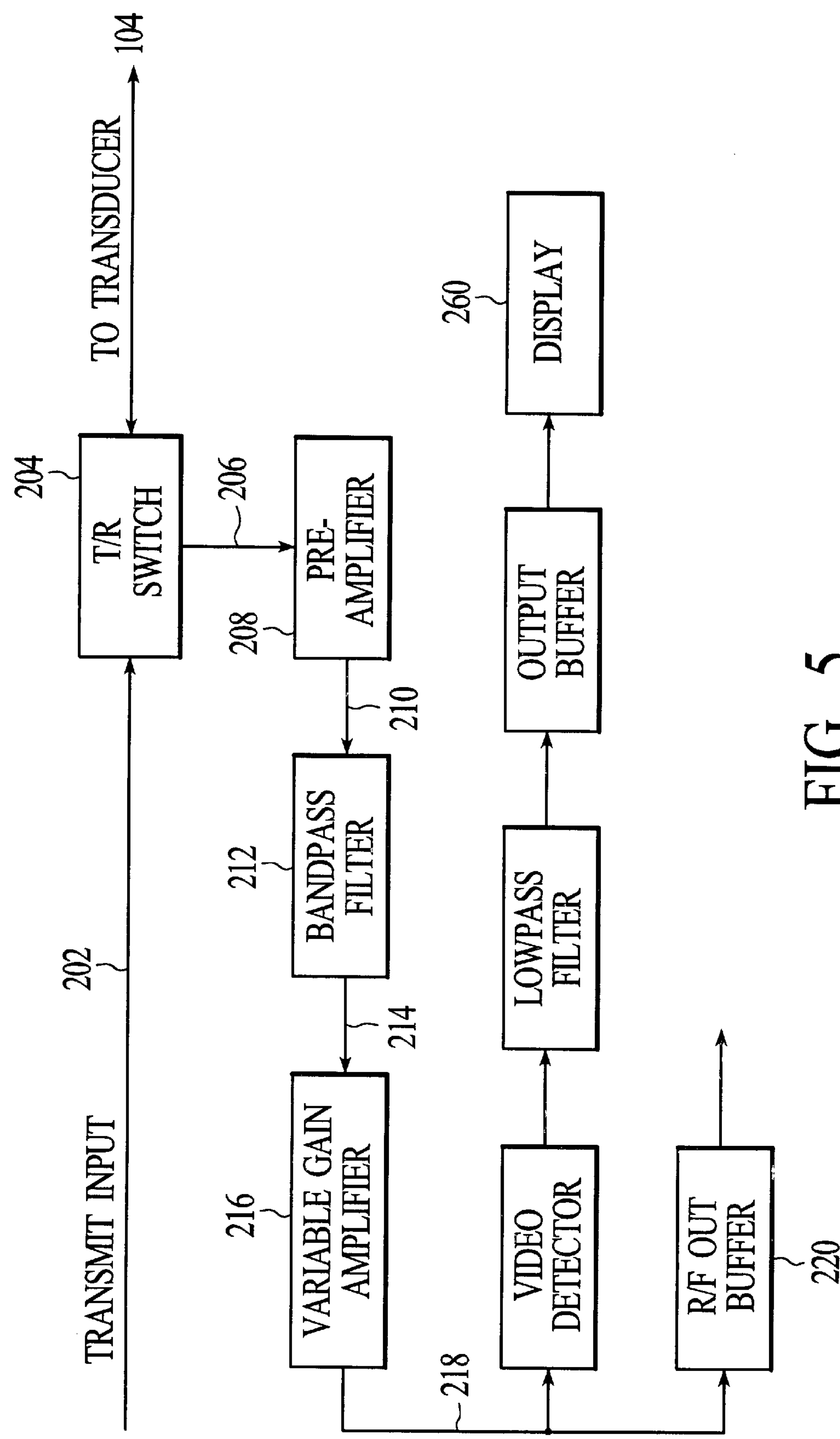
FIG. 5 is a representative electrical schematic RF module block diagram of a preferred embodiment of an ultrasound guidance system.

FIG. 5 is a representative electrical schematic RF module block diagram of a preferred embodiment of an apparatus. Excitation of the ultrasound transducer 104 is caused by input signal 202. Input signal 202 is switched to the ultrasound transducer 104 through transmit and receive (T/R) switch 204. The transducer 104 emits a signal in response to every input signal 202. Signals 206 from transducer 104 and echoes are converted to signals which are switched through T/R switch 204 to pre-amplifier 208. Filtering of the amplified signals 210 by bandpass filter 212 and further processing and amplification of the filtered signals 214 by variable gain amplifier 216 produce selected amplified signals 218 containing information about depth of structure, such as myocardium, which can be further processed as desired.

As shown, such selected amplified signals 218 can be received by $RF_{out}$ buffer 220 for recording the information, etc. A video detector sufficient to cover the range of possible frequencies used in the ultrasound system, such as between about 5 and 20 MHz and more preferably about 15 MHz, provides a signal used to create an A-mode scan for viewing on display 260. It will be understood that the display means 260 can be an oscilloscope, computer monitor, or can be input to a computer and stored. It will further be understood that software processing of emitted pulse data and echo data to calculate signal delay, for determination of depth to a tissue boundary surface, or depth of myocardium from wall to wall, can be achieved using various or custom software.

Figure 7:
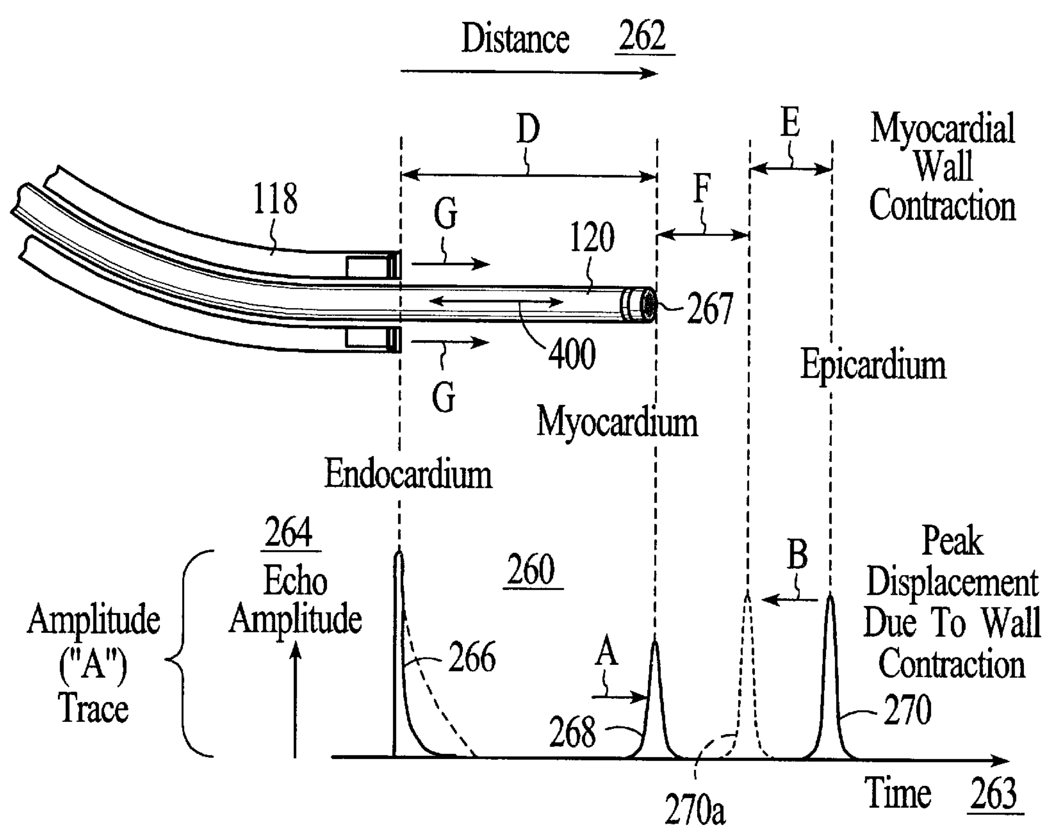
FIG. 7 is a representative A-mode scan display in juxtaposition with a representation with a method of use of a preferred embodiment of an ultrasound guidance.

FIG. 7 is a representative A-mode scan display 260 in juxtaposition with a representation of the method of use of a preferred embodiment of an apparatus for TMR, discussed further below. It will also be understood that FIG. 7 refers to an ultrasound ranging device comprising a catheter for percutaneous surgery, and the application is TMR from inside the left ventricle into the myocardium. The residual signal from the transmitted impulse various depending on the location of distal tip 102 and the shape of the echo amplitude curve changes when the distal tip 102 is up against the endocardium or whether it is free in the left ventrical. Dampening is different if the distal end 102 is in contact with the wall. In FIG. 7, the dotted line indicates that the distal end 102 is free in the left ventricle as compared to be positioned at the wall as indicated by the solid line.

One Embodiment of a Preferred Methodology

It is well understood that the time for return of an echo from a distance D is given by the following equation:

$$t = 2\frac{d}{V_s} \quad (1)$$

where $V_s$ is the velocity of longitudinal sound waves, i.e., approximately 1540 m/s in myocardial tissue. Therefore, algorithms for generating the A trace consist of detecting the envelope of the received RF signal. These algorithms are known in the areas of echo ranging with ultrasound and radar. In a preferred embodiment, the analytic magnitude is used, which consists of computing the Fourier transform, taking the real part of the result, and computing the inverse Fourier transform. If the original echo signal is called f(t), then the amplitude A(t) is computed according to the following equation:

$$A(t) = \int_{\infty}^{-\infty} e^{-izt} R_e\left\{\int_{\infty}^{-\infty} e^{izt} f(t)dt\right\}dz \quad (2)$$

Figure 8:
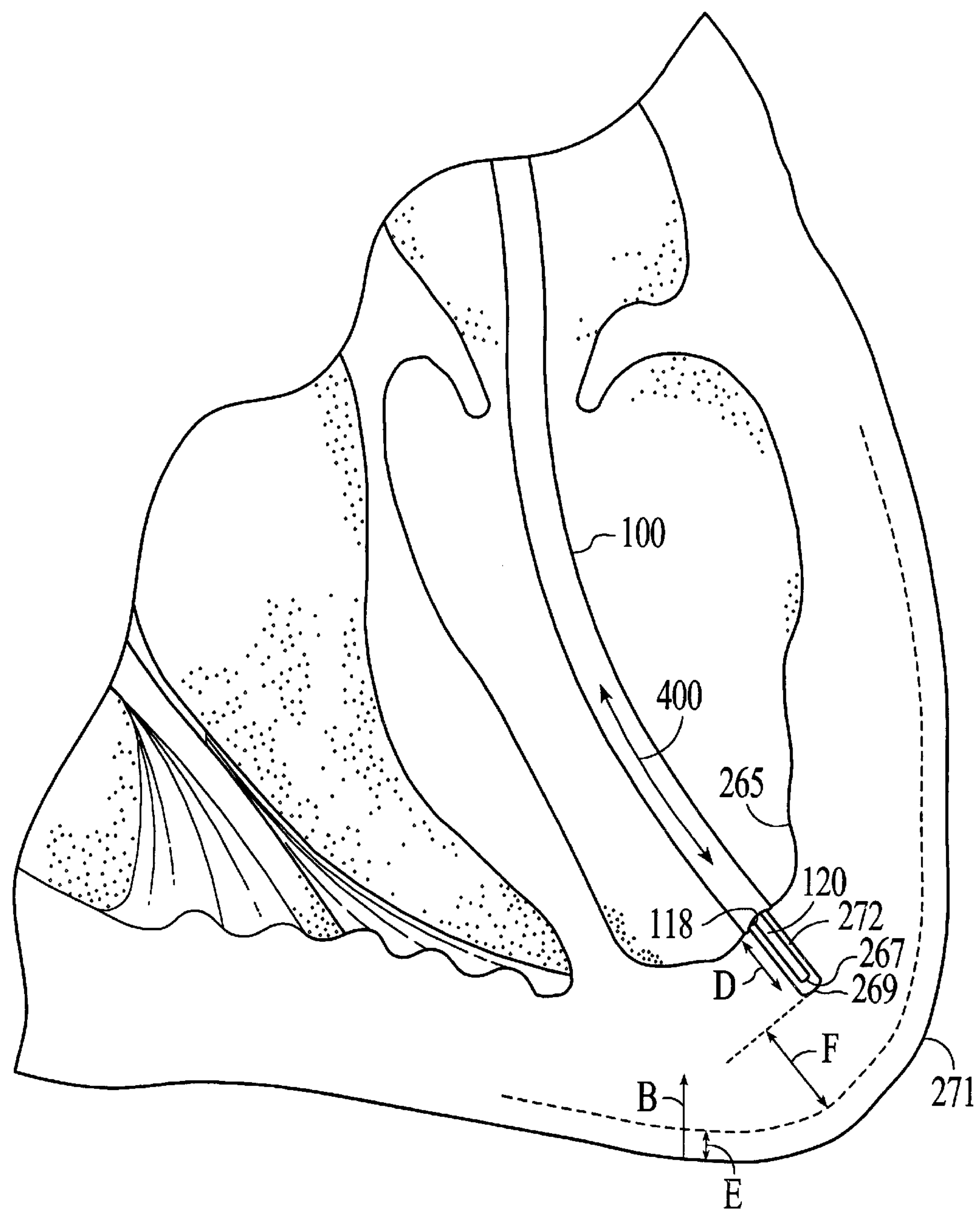
FIG. 8 is a representative drawing of a preferred method of use of a preferred embodiment of the apparatus.

Referring again to FIG. 7 as well as to FIG. 8, forward viewing distance 262 is shown on the X-axis and the amplitude of the reflected or echo signal 264 is plotted on the Y-axis. Distance 262 is also correlated with time 263. A first strong amplitude peak 266 is associated with the endocardial surface 265, such surface also referred to herein as a boundary surface of tissue. When the transducer is in contact with an endocardial surface 265 (not shown in FIG. 7), such surface 265 will be visualized by initial amplitude peak 266. As the laser delivery means 120 is fired, ablation of tissue occurs, and the distal tip 267 of the laser delivery means 120 can be moved forward into the tissue. Continued ablation creates a channel 272 (see FIG. 8) into which the distal tip 267 of the laser delivery means 120 advances for continued channel 272 creation. Thus, a second highly observable amplitude peak 268 on the ultrasound A-mode scan display 260 is formed by the echo returning from the end of the channel 269, and the distal tip 267 of laser delivery means 120, within myocardium. This second peak 268 will be observed to move from left to right, as shown by directional arrow A, as laser ablation and TMR channel 272 formation occurs.

An additional peak 270 is observable at the right side of the display 260. As the ultrasound wave propagates through the tissue, an additional returning echo signal will indicate a structural interface or tissue boundary surface at the position which correlates with the distance to the back wall of the penetrated structure 271, i.e., in this case, the epicardial surface 271 of the heart. However, as is well known, the contractions of the beating heart will tend to cause the wall of the heart to contract in direction B, as well as expand in the opposite direction, thereby causing the wall peak 270 to move in direction C. Thus, an additional wall peak 270*a* will be observable, which will be a transient peak moving between the positions indicated for peaks 270 and 270*a*. Thus, as shown, the distance D can be correlated with the length of the channel 272 and the distance E can be correlated with the distance moved by the epicardial surface 271 during contraction of the heart muscle. Therefore, it will be understood that distance F will be correlated with the amount of remaining myocardial tissue between the end of the TMR channel 269 and the epicardial surface 271. This information regarding remaining depth of tissue is vital to the cardiologist in performing TMR. With regard to percutaneous TMR, by controllably forming TMR channels initiating at an endocardial surface, perforation of the epicardium can be avoided.

The apparatus 100 will be usefully operated at pulse repetition frequencies between about 100 Hz and about 10 KHz. Such frequencies will be fast enough to allow real-time display of the thickening and thinning of the heart wall brought about as a result of the changes between the systole and diastole components of the beating heart cycle.

Figure 9:
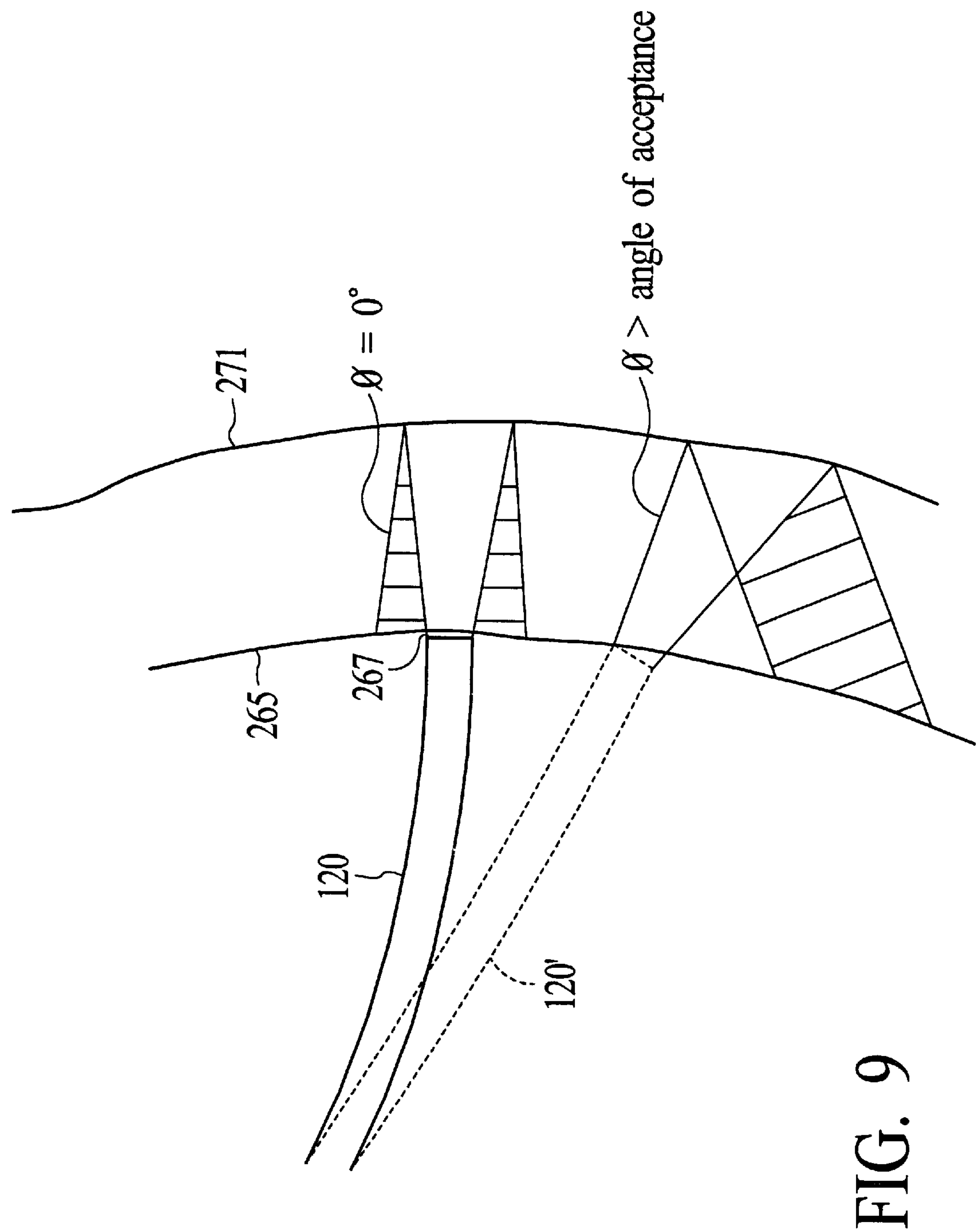
FIG. 9 shows a comparison between the wall thickness or channel depth at 90° or other angulation.

As illustrated in FIG. 9, the apparatus 100 can also be used to determine the perpendicularity of the contact between the apparatus 100 and a tissue surface. The angle at which the apparatus 100 approaches a tissue surface is called the angle of approach, defined as the angle between the axis of distal tip 102 and a perpendicular (or normal) to the surface, at the point of intersection between the axis and the surface. The apparatus 100 is designed to have an angle of acceptance which is the angle that the apparatus 100 can approach a tissue surface while still receiving an ultrasound echo. In the image with the solid line in FIG. 9, the angle between the longitudinal axis of the distal tip 102 and the normal to the tissue surface is zero degrees. In various embodiments, the angle between the longitudinal axis of the distal tip 102 and the normal to the tissue surface is 30° or less, 20° or less, and 10° or less.

Referring now to FIG. 10(*a*), a portion of distal tip 102 is in physical contact with a heart tissue front boundary surface. The angle between the longitudinal axis of the distal tip 102 and the normal to the front boundary surface is 30° or less and a returning echo from the rear boundary surface is detected. In this manner, the depth of the tissue surface at the point of contact between distal tip 102 and the front boundary surface is determined. In FIG. 10(*b*), the distance between distal tip 102 and the front boundary surface is determined prior to contact. Finally in FIG. 10(*c*), the angle between the longitudinal axis of the distal tip 102 and the normal to the front boundary surface is too large and the return echo from the back boundary surface is not detected.

When the angle between the longitudinal axis of the device and a line perpendicular to the tissue surface is larger than the angle of acceptance of the apparatus 100, the reflected echo signal will not impinge on the transducer 104, resulting in no signal on the display. Since it is preferable to have contact occur within a limited angular range in order to ensure penetration, the lack of echo signal is interpreted as improper positioning, thus avoiding the firing of the laser means under unfavorable conditions.

Referring to FIG. 8, another modality of operation of the apparatus 100 is referred to as retrolasing. In retrolasing, the catheter, MIS or other surgical device preferably has a piercing tip. In the context of percutaneous TMR in the left ventricle, retrolasing is accomplished by inserting the distal tip 267 of the laser delivery means 120 through a mechanically formed perforation in the endocardium 265. The distal tip 267 is advanced a selected distance D into myocardium and the location of the distal tip 267 is confirmed using the apparatus 100, such as by visualization on an oscilloscope, computer monitor or other display means, as shown in FIG. 7. Once the tip 267 is placed where desired and the placement confirmed on the ranging display means, laser delivery can commence, firing the laser will initiate creation of a TMR channel 272 and the firing tip 267 is retracted simultaneously with viewing and continued delivery of laser energy. Additionally, the laser can be configured to automatically fire only upon confirmation of a threshold depth measurement setting, taking into account the fluctuating wall thickness due to the contractions of the heart. Not only will this enable retrolasing starting at an initial depth of penetration into myocardium, as confirmed by computer software or logic, but it will also confirm normal heart function, i.e., beating of the heart.

As another method for confirming and/or controlling specific heart function, pacing of the heart has been described. When pacing the heart with an external pulse generator during a TMR procedure, there is often no positive confirmation that the heart has beat properly or even at all. Therefore, this positive confirmation of heart function, albeit compromised or otherwise imperfect, may be accomplished by using the ultrasound ranging device and methods described herein to detect the heart beat. The ultrasound device could monitor the measured thickness of the myocardium and determine when a change has occurred. The change in thickness of myocardium can be correlated with contraction and/or expansion of the heart. This signal indicating that the heart has beat could be used such that the TMR laser would not fire unless and until this signal is received. Such pacing of the heart is more fully described in co-pending U.S. patent application Ser. No. 16684-702], filed Feb. 3, 1997 entitled "REVASCULARIZATION WITH HEART PACING", as well as U.S. patent application Ser. No. , filed concurrently therewith entitled "REVASCULARIZATION WITH LASER BURSTS AND REVASCULARIZATION WITH HEARTBEAT VERIFICATION", both of which are incorporated herein by reference.

Therefore, when a device or method in which a pre-set number of laser pulses, such as a burst of 5 pulses, is used to create the TMR channels, that pre-set number of pulses can be automatically reduced when heart wall thicknesses are reduced to below a predetermined threshold, such as 5 millimeters. This heart wall thickness measurement can be made in essentially real time by the axial ranging devices and methods of using the apparatus 100.

One embodiment of apparatus 100 shows real time indications of wall thickness as well as thickness changes during the cardiac cycle. Additionally, apparatus 100 can be used to measure the thickness during a fixed period of the cardiac cycle. Further, the ultrasound transmission of apparatus 100 can be synchronized to the ECG signal from the patient. Synchronization allows the signal to reduce the effect of the cardiac cycle on the readings from a ranging system.

Figure 6:
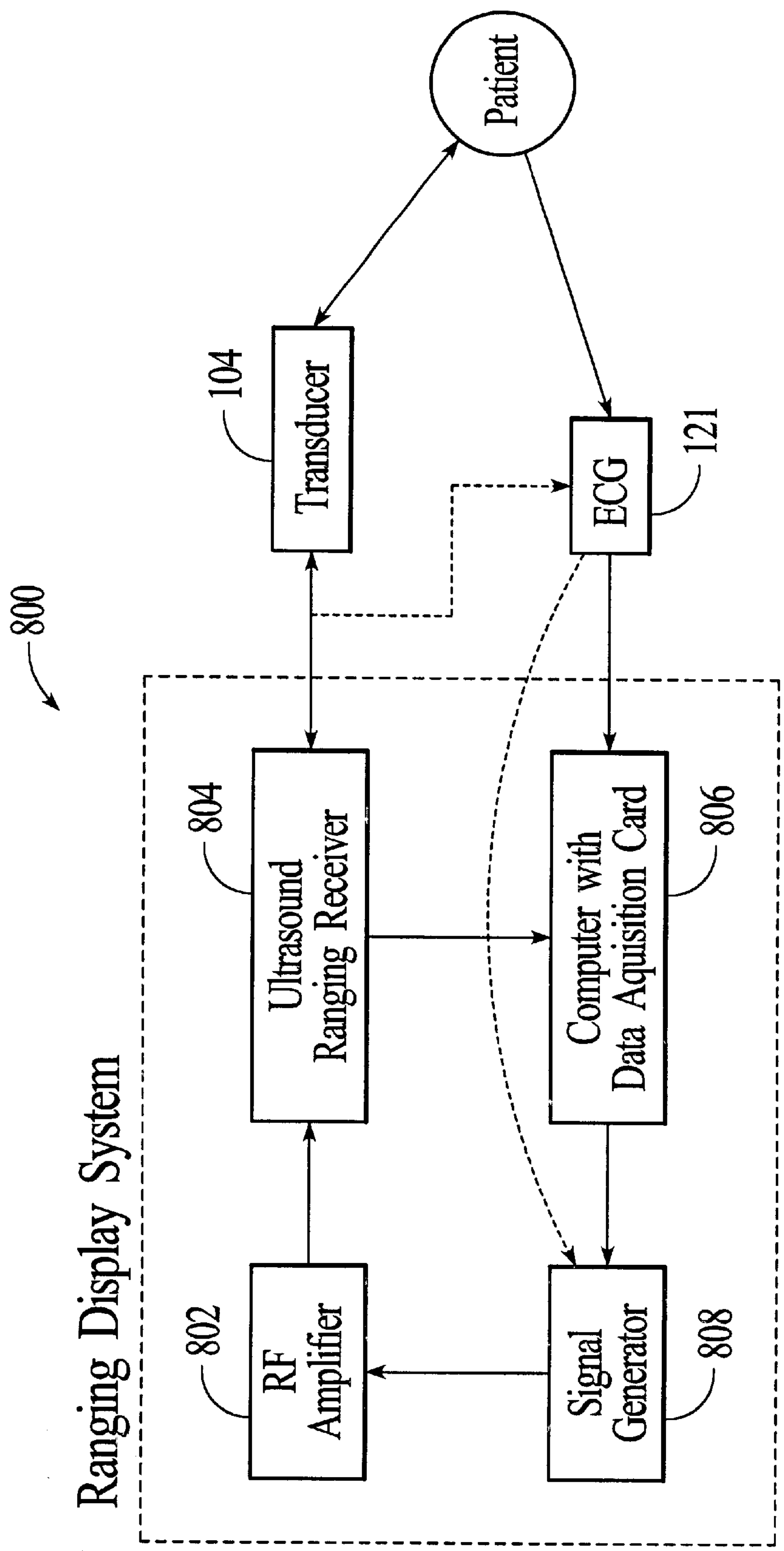
FIG. 6 is a block diagram of a system with a transducer and an electrode coupled with a processing unit.

Referring now to FIG. 6, a ranging display system 800 interfaces with a ranging catheter 100 to provide an indication of the thickness of the myocardium at the point at which it is contacted by the catheter distal tip 102, and an indication of the distance from the distal tip 102 of the fiber optic to the catheter distal tip 102. Ranging display system 800 includes an RF amplifier 802, an ultrasound ranging receiver 804, a computer with data aquisition card 806. Transducer 104 is coupled to ultrasound ranging receiver 804 and ECG 121. ECG 121 is coupled to computer with data aquisition card 806.

In one specific embodiment of ranging display system 800, an HP3314 signal generator creates a pulse of RF energy. This pulse can be 12 MHz sine wave with an amplitude of 100 mV peak to peak. The duration of the pulse is 8 complete cycles or 667 nsec and the repetition frequency is 100 Hz. The computer controls the initialization and setup of parameters for the signal generator via a GPIB bus. The signal is amplified by an ENI RF amplifier which has a gain of 50 dB. This generates a signal with a peak power of 2.5 watts (with a transducer impedance of 50 ohms). The amplified signal is transmitted to the connector on the front of the unit to which the transducer 104 is connected.

Echos are returned from the transducer 104. These echos will correspond to either the epicardium or the distal tip of the fiber. The signals from the transducer 104 are amplified and filtered through an RF receiver and digitized. The gain is selected by the operator. The filter in the receiver has a 12 MHz center frequency and a 3 MHz 3 dB bandwidth. The amplified and filtered signals are digitized using an 8 bit, 40 MHz data acquisition system.

A computer controls the setup and initialization of the signal generator, and reads the signals from the data acquisition system. The processing of the digitized signals includes rectification, peak detection and temporal and spatial filtering. The processed signals are displayed on the LCD and comprise the A-trace data.

Several algorithms exist for generating an A-trace which is the envelope of the received RF signal (f(f)) from an ultrasound system. The sample algorithms include:

$$A_1(t) = \sqrt{f^2(t)} \tag{3}$$

$$A_2(t) = |f(t)| \tag{4}$$

additionally, a conventional solution exists in which the A-trace is calculated as follows:

$$A_3(t) = \int_{-\infty}^{\infty} e^{-izt} Re\left\{\int_{-\infty}^{\infty} e^{izt} f(t)dt\right\}dz \tag{5}$$

An alternative algorithm is as follows:

$$A_4(t) = \sqrt{f^2(t) + f^2(t - \Delta T)} \tag{6}$$

where ΔT is chosen to be an integer multiple of the sample period. This algorithm has the advantage of easy computation similar to equation (3) and better performance approaching equation (5). This method will give similar results to the optimal algorithm (5) in the case where the sample rate is equal to a multiple of 4× the fundamental frequency of the RF and the frequency of the envelope wave form is low in comparison to the fundamental frequency. In order to maintain the optimal performance a variable sample rate could be implemented to maintain the preferred relationship. In each case the parameter ΔT is chosen to as close to $(1/4)(1/f_{rf})$ where $f_{rf}$ is the fundamental frequency. This gives a delay of 90° in phase between the two samples used in the equation.

Algorithm for Processing Ultrasound Echos #2

A computer simulation was performed in which a ramp function modulated by a fundamental frequency ($f_{rf}$) is sampled at a 40 MHz rate and processed by algorithm 6. The output of the algorithm is compared to the input wave form and a RMS error is computed. This simulation was repeated for frequencies from 9–16 MHz and ΔT=1, 1 and Z × the sample interval. For ΔT=O the algorithm is equivalent to equation (1) and is used as a baseline for comparison. The table below shows the results of the simulation.

| $f_{rf}$ | RMS Error ΔT = 0 | RMS Error ΔT = $1T_s$ | RMS Error ΔT = $2T_s$ | Error % |
|---|---|---|---|---|
| 9 | .223 | .031 | .199 | 13.9 |
| 10 | .377 | .015 | .377 | 3.9 |
| 11 | .223 | .030 | .199 | 13.4 |
| 12 | .251 | .056 | .156 | 22.3 |
| 13 | .220 | .083 | .110 | 37.7 |
| 14 | .228 | .107 | .060 | 26.3 |
| 15 | .266 | .129 | .026 | 9.77 |
| 16 | .250 | .153 | .059 | 23.6 |

The table includes values of ΔT=0, $1T_s$ and $2T_s$ where $T_s$=the sampling interval. The % error is calculated by comparing to the baseline values (ΔT=0). For the higher fundamental frequencies (ff greater than 12 MHz), a delay of $2\times T_s$ gives a lower error than $1\times T_s$ and the algorithm could choose the desired delay as a function of frequency. This comparison shows that for the non-optimal fixed sample frequency case the RMS error is reduced to at worst 37% of algorithm (1). An advantage of the above formulae are the provision of a smooth signal with rapid processing which allows for an increased sampling rate and variable sampling.

Advantages of the preceding embodiment include improved accuracy, ease of use and implementation with a need for a less powerful computer, a higher process flow rate, an increase in sampling rate with a fixed amount of memory and higher resolution and ease in writing the code.

By the present disclosure, it will be apparent to those skilled in the art that audible or visual alarms may be incorporated into the apparatus 100. Audible or visual alarms will give the cardiologist advance notice of achievement of threshold TMR channel depth penetration. Such alarms can also be integrated with mechanical as well as electronic interlock systems for the laser, thereby enhancing efficacy and safety of the apparatus 100 and methods described herein. Thus, the apparatus 100 may also be configured to include means to automatically stop fiber advance based on the calculated or otherwise determined axial distance of the firing tip of the laser delivery means from the back wall. Such means includes, but is not limited to mechanically or electronically controlled interlock with feedback loop, electrophysiology signal, etc. The present invention will assist the cardiologist in visualizing the tip of the catheter or surgical apparatus and the distal tip of the laser delivery means, as well as the endocardial wall, in a percutaneous, intra-ventricle procedure, so that identification of contact between the distal tip of the apparatus 100 or laser delivery means and the heart surface can be made. Such contact identification will allow the operator or cardiologist to avoid applying excessive force upon the heart, and thus avoid excessive arrhythmagenic forces thereby.

The present invention is intended for use with any medical laser. In particular, the Holmium, YAG or excimer lasers are particularly suited to the present invention. However, any suitable laser source, pulsed or otherwise, could provide laser energy to the laser delivery means for performing the disclosed methods. Furthermore, other interventional systems, in addition to lasers, which are included within the scope of the apparatus 100, other radio frequencies thermal or mechanical intervention. Based on the disclosure herein, control of these types of interventional modalities will be known to those skilled in the art.

Likewise, the catheter and surgical equipment, including laser delivery means, referred to in the present document as well as that known and used in medicine and other disciplines today and in the future, will be included in the scope of this disclosure. Such laser delivery means include, but are not limited to, individual optical fibers, fibers or fiber bundles with lens tips as well as bundles of fibers with and without piercing tips and with or without firing tips, fiber ends having shaped or contoured end faces for selectively diverging the laser beam or other laser energy diverging means, rods, mirrors configurations and other laser delivery means with and without focusing lens and the like. It will also be understood that the apparatus and method as described herein including the novel combination or use with of any conventional mechanism or method which are known to those skilled in the art, are included within the scope of this invention. Furthermore, with regard to non-laser TMR, a cannula or trocar assembly may be extended into the tissue of the left ventricle, with or without use of a mechanical piercing tool.

It will further be understood that while the present invention has been described for performing TMR on endocardial surfaces in the left ventricle, the apparatus and methods described herein are equally intended for use in any suitable procedure, including but not limited to procedures where any device need be extended through a guide catheter to a given surface on a given structure and extended into the structure a selected and controlled distance, for any medical procedures including laser treatment, tissue or organ visualization, biopsy, etc. AStimulation@, for example, is performed by using laser energy to create zones or pockets, optionally interconnected at least initially by small channels ablated through the tissue, for the introduction of blood born growth and healing factors and stimulated capillary growth surrounding the lased zones or pockets to create an increased supply of oxygen to the tissue and thus a revitalization of the heart muscle. Methods and apparatus for causing stimulation are more fully described in co-pending U.S. patent application Ser. No. 08/664,956 filed Jun. 13, 1996.

The present invention is applicable to TMR, stimulating angiogenesis, introducing an angiogenesis stimulation agent, determining that location of a distal portion of a catheter or other surgical device relative to a surface of a targeted body structure, and the like.

Suitable angiogenesis stimulation agents include recombinant proteins, specific inhibitors of protein-protein interactions, tyrosine kinase inhibitors, gene transfer agents and the like. More specifically, the angiogenesis stimulation agent can be a basic fibroblast growth factor (bFGF) or a vascular endothelial growth factor (VEGF).

The FGF growth factor family includes eight structurally-related polypeptides: basic FGF, acidic FGF, int 2, hst 1/k-FGF, FGF-5, FGF-6, keratinocyte growth factor, AIGF (FGF-8) and a glia-activating factor, heparin-binding growth factor purified from the culture supernatant of a human glioma cell line, (Miyamoto, M. et al., Mol. and Cell. Biol., 13(7):4251–4259 (1993). The genes for each are cloned and sequenced. FGF-1 and FGF-2 are characterized as acidic and basic fibroblast growth factors.

EXAMPLE 1

Bacterial Expression and Purification of FGF-13 Protein

The DNA sequence encoding FGF-13 ATCC #97148, is initially amplified using PCR oligonucleotide primers corresponding to the 5' sequences of the processed protein (minus the signal peptide sequence) and the vector sequences 3' to the gene. Additional nucleotides corresponding to the gene are added to the 5' and 3' sequences respectively. The 5' oligonucleotide primer 5' GCCAGACCATGGAGAATCACCCGTCTCCTAAT 3' (SEQ ID NO:3) contains a Nco restriction enzyme site. The 3' sequence 5' GATTTAAGATCTCGTGAGGGGCTGGGGCCG3' (SEQ ID NO:4) contains complementary sequences to a BglII site and is followed by 18 nucleotides of FGF-13 coding sequence.

The restriction enzyme sites correspond to the restriction enzyme sites on the bacterial expression vector pQE-60 (Qiagen, Inc. Chatsworth, Calif.91311). pQE-60 encodes antibiotic resistance (Ampr), a bacterial origin of replication (ori), an IPTG-regulatable promoter operator (P/O), a ribosome binding site (RBS), a 6-His tag and restriction enzyme sites. pQE-60 was then digested with NcoI and BglII. The amplified sequences are ligated into pQE-60 and are inserted in frame with the sequence encoding for the histidine tag and the ribosome binding site (RBS). The ligation mixture is then used to transform *E. coli* strain M15/rep 4 (Qiagen, Inc.) by the procedure described in Sambrook, J. et al., Molecular Cloning: A Laboratory manual, Cold Spring Laboratory Press, (1989). M15/rep4 contains multiple copies of the plasmid pREP4, which expresses the lacI repressor and also confers kanamycin resistance (KaW). Transformants are identified by their ability to grow on LB plates and ampicillin/kanamycin resistant colonies were selected. Plasmid DNA is isolated and confirmed by restriction analysis. Clones containing the desired constructs are grown overnight(O/N) in liquid culture in LB media supplemented with both Amp (100 ug/ml)and Kan (25 ug/ml). The O/N culture is used to inoculate a large culture at a ratio of 1:100 to 1:250. The cells are grown to an optical density 600(O. D. sup 600) of between 0.4 and 0.6. IPTG ("Isopropyl-B-D-thiogalactopyranoside") is then added to a final concentration of 1 mM. IPTG induces by inactivating the lacI repressor, clearing the P/O leading to increased gene expression. Cells are grown an extra 3 to 4 hours. Cells are then harvested by centrifugation. The cell pellet is solubilized in the chapotropic agent 6 Molar Guanidine HCl. After clarification, solubilized FGF-13 is purified from this solution by chromatography on a Nickel-Chelate column under conditions that allow for tight binding by proteins containing the 6-His tag (Hochuli, E. et al., J. Chromatography 411:177–184 (1984)). The proteins are eluted from the column in 6 molar guanidine HCl pH 5.0 and for the purpose of renaturation adjusted to 3 molar guanidine HCl, 100 mM sodium phosphate, 10 mm olar glutathione (reduced) and 2 mmolar glutathione (oxidized). After incubation in this solution for 12 hours the proteins are dialyzed to 10 mmolar sodium phosphate.

EXAMPLE 2

Expression via Gene Therapy

Fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature over night. After 24 hours at room temperature, the flask is inverted and the chunks of tissue remain fixed to the bottom of the flask and fresh media (e.g., Ham's F12 media, with 10% FBS, penicillin and streptomycin, is added. This is then incubated at 37 degree(s) C. for approximately one week. At this time, fresh media is added and subsequently changed every several days. After an additional two weeks in culture, a monolayer of fibroblasts emerge. The monolayer is trypsinized and scaled into larger flasks.

pMV-7 (Kirschmeier, P. T. et al, DNA, 7:219–25 (1988) flanked by the long terminal repeats of the Moloney murine sarcoma virus, is digested with EcoRI and HindIII and subsequently treated with calf intestinal phosphatase. The linear vector is fractionated on agarose gel and purified, using glass beads. The cDNA encoding a polypeptide of the present invention is amplified using PCR primers which correspond to the 5' and 3' end sequences respectively. The 5' primer containing an EcoRI site and the 3' primer having contains a HindIII site. Equal quantities of the Moloney murine sarcoma virus linear backbone and the EcoRI and Himd III fragment are added together, in the presence of T4 DNA ligase. The resulting mixture is maintained under conditions appropriate for ligation of the two fragments. The ligation mixture is used to transform bacteria HB101, which are then plated onto agar-containing kanamycin for the purpose of confirming that the vector had the gene of interest properly inserted.

The amphotropic pA317 or GP+am 12 packaging cells are grown in tissue culture to confluent density in Dulbecco's Modified Eagles Medium (DMEM) with 10% calf serum (CS), penicillin and streptomycin. The MSV vector containing the gene is then added to the media and the packaging cells are transduced with the vector. The packaging cells now produce infectious viral particles containing the gene (the packaging cells are now referred to as producer cells). Fresh media is added to the transduced producer cells, and subsequently, the media is harvested from a 10 cm plate of confluent producer cells. The spent media, containing the infectious viral particles, is filtered through a millipore filter to remove detached producer cells and this media is then used to infect fibroblast cells. Media is removed from a sub-confluent plate of fibroblasts and quickly replaced with the media from the producer cells. This media is removed and replaced with fresh media. If the titer of virus is high, then virtually all fibroblasts will be infected and no selection is required. If the titer is very low, then it is necessary to use a retroviral vector that has a selectable marker, such as neo or his.

The engineered fibroblasts are then injected into the host, either alone or after having been grown to confluence on cytodex 3 microcarrier beads. The fibroblasts now produce the protein product.

EXAMPLE 3

Synthesis of the bFGF Amino Acid Residue

To synthesize a protein having the mammalian bFGF amino acid residue sequence by recombinant DNA, a double-stranded DNA chain which encodes bFGFs synthetically constructed. In addition to the bFGF-encoding sequences, the DNA chain that is synthesized may contain additional sequences, depending upon vector construction considerations. Typically, the DNA chain is synthesized with linkers at its ends to facilitate insertion into restriction sites within a cloning vector. The DNA chain may be constructed so as to encode the bFGF amino acid sequences as a portion of a fusion polypeptide; and if so generally contains terminal sequences that encode amino acid residue sequences that serve as proteolytic processing sites, whereby the bFGF polypeptide may be proteolytically cleaved from the remainder of the fusion polypeptide. The terminal portions of the synthetic DNA chain may also contain appropriate start and stop signals.

To assemble a bFGF-encoding DNA chain, oligonucleotide are constructed by conventional methods, such as procedures described in T. Manatis et al., Cold Spring Harbor Laboratory Manual, Cold Spring Harbor, N.Y. (1982) (hereinafter, CSH). Sense and antisense oligonucleotide chains, up to about 70 nucleotide residues long, are synthesized, preferably on automated synthesizers, such as the Applied Biosystem Inc. model 380A DNA synthesizer. The oligonucleotide chains are constructed so that portions of the sense and antisense oligonucleotide overlap, associating with each other through hydrogen binding between complementary base pairs and thereby forming double stranded chains, in most cases with gaps in the strands. Subsequently, the gaps in the strands are filled in and oligonucleotides of each strand are joined end to end with nucleotide triphosphates in the presence of appropriate DNA polymerases and/or with ligases.

As an alternative to construction of a synthetic DNA chain through oligonucleotide synthesis, cDNA corresponding to bFGF may be prepared. AcDNA library or an expression library is produced in a conventional manner by reverse transcription from messenger RNA (mRNA) from a bFGF-producing mammalian cell line. To select clones containing bFGF sequences, hybridization probes (preferably mixed probes to accommodate the degeneracy of the genetic code) corresponding to portions of the bFGF protein are produced and used to identify clones containing such sequences. Screening of the expression library with bFGF antibodies may also be used, alone or in conjunction with hybridization probing, to identify or confirm the presence of bFGF-encoding DNA sequences in DNA library clones.

The double-stranded bFGF-encoding DNA chain is constructed or modified with insertion into a particular appropriate cloning vector in mind. The cloning vector that is to be recombined to incorporate the DNA chain is selected appropriate to its viability and expression in a host organism or cell line, and the manner of insertion of the DNA chain depends upon factors particular to the host. For example, if the DNA chain is to be inserted into a vector for insertion into a prokaryotic cell, such as *E.coli*, the DNA chain will be inserted 3' of a promoter sequence, aShine-Delgarno sequence (or ribosome binding site) that is within a 5' non-translated portion and an ATG start codon. The ATG start codon is appropriately spaced from the Shine-Delgarno sequence, and the coding sequence is placed in correct reading frame with the ATG start codon. The cloning vector also provides a 3' non-translated region and a translation termination site. For insertion into a eukaryotic cell, such as a yeast cell or a cell line obtained from a higher animal, the bFGF-encoding oligonucleotide sequence is appropriately spaced from a capping site and incorrect reading frame with an ATG start signal. The cloning vector also provides a 3' non-translated region and a translation termination site.

Prokaryotic transformation vectors, such as pBR322, pMB9, Col E1, pCR1, RP4 and lambda-phage, are available for inserting a DNA chain of the length which encodes bFGF with substantial assurance of at least some expression of the encoded polypeptide. Typically, such vectors are constructed or modified to have a unique restriction site(s) appropriately positioned relative to promoter, such as the lac promoter. The DNA chain may be inserted with appropriate linkers into such a restriction site, with substantial assurance of production of bFGF in a prokaryotic cell line transformed with the recombinant vector. To assure proper reading frame, linkers of various lengths may be provided at the ends of the bFGF-encoding sequences. Alternatively, cassettes, which include sequences, such as the 5' region of the lac Z gene (including the operator, promoter, transcription start site, Shine Delgarno sequence and translation initiation signal), the regulatory region from the tryptophane gene (trp operator, promoter, ribosome binding site and translation initiator), and a fusion gene containing these two promoters called the trp-lac (Tac) promoter are available into which the synthetic DNA chain may be conveniently inserted and then the cassette inserted into a cloning vector of choice.

Similarly, eukaryotic transformation vectors, such as the cloned bovine papilloma virus genome, the cloned genomes of the murine retro viruses, and eukaryotic cassettes, such as the pSV-2 gpt system (described by Mulligan and Berg, Nature 277, 108–114, 1979) the Okayama-Berg cloning system (Mol.Cell Biol., 2: 161–170, 1982), the expression cloning vector described by Genetics Institute (Science 228: 810–815, 1985), are available which provide substantial assurance of at least some expression of bFGF in the transformed eukaryotic cell line. Production of bFGF or a polypeptide of a similar length can be achieved by producing the polypeptide initially as a segment of a gene-encoded fusion polypeptide. In such case, the DNA chain is constructed so that the expressed polypeptide has enzymatic processing sites flanking the bpFGF amino acid residue sequences. A bFGF-encoding DNA chain may be inserted, for example, into the beta-galactosidase gene for insertion into *E. coli*, in which case, the expressed fusion polypeptide is subsequently cleaved with proteolytic enzymes to release the bFGF from beta-galactosidase peptide sequences.

EXAMPLE 4

Determination of Bovine bFGF

Frozen bovine pituitaries are homogenized with a Waring blender for 5 minutes in 0.15M ammonium sulfate (4 liter/kg tissue). The pH is adjusted to 4.5 with HCl and the homogenate stirred vigorously for 2 hours. After centrifugation (18,000×g, 30 minutes) the supernatant is retained. 230 g ammonium sulfate per liter of supernatant are added, the pH is adjusted to 6–6.5 with NaOH and the precipitation is allowed to proceed for 15 hours. After centrifugation of the reaction mixture (18,000×g, 30 min), the supernatant is retained. 300 g ammonium sulfate is added to each liter of the supernatant. The mixture is stirred for two hours. After centrifugation of the reaction mixture (18,000×g, 30 min) the pellet is retained, and the cumulative pellets from 3 kg starting tissue dissolved in 200 ml distilled water and dialyzed against 20 liters of distilled water overnight. The pH of the dialyzed retentate is then adjusted to 6, and the solution clarified by centrifugation (12,000×g, 30 min). The dialyzed retentate constitutes a dialyzed extract.

Basic FGF is subsequently isolated from the dialyzed, clarified extract using three successive protocols. Two of the protocols employ conventional ion-exchange and reverse phase HPLC purification steps. The third method uses heparin-Sepharose affinity chromatography in a key purification step as detailed as follows in the order in which they are performed.

(A) CM-Sephadex (C50) Ion-Exchange Chromatography

A 7×9 cm column of carboxymethyl Sephadex (C50) is washed with 1 liter of 50 mM sodium phosphate, 1.5M sodium chloride, pH 6.0 and then equilibrated with 0.1M sodium phosphate, pH 6 slashed zero. The dialyzed extract from 3 kg bovine pituitaries is loaded onto the column, and the column is washed sequentially with 0.1M sodium phosphate, pH 6.0 containing a) no NaCl, b) 0.2M NaCl and c) 0.65M NaCl, allowing the OD sub 280 to reach a minimum value before initiating each new wash. Fractions of 18 ml are collected at 3 ml/min at 4 degree(s) C. and subjected to radioimmunoassay.

(B) Heparin-Sepharose Chromatography

The 0.65M NaCl eluate from CM-Sephadex chromatography is loaded onto a 3×3 cm column of heparin-Sepharose (Pharmacia) previously equilibrated with 10 mM Tris-HCl, 0.6M NaCl, pH 7.0 at room temperature. The column is then washed sequentially with 10 mM Tris-HCl, pH 7.0 containing a) 0.6M NaCl and b) 1.1M NaCl, allowing the $OD_{280}$ to reach a minimum value with each wash. The basic FGF is then eluted with a linear gradient in 10 mM Tris-HCl, pH 7.0 containing 100 ml 1.1M NaCl and 100 ml 2M NaCl. Fractions of 5 ml are collected at 0.8 ml/min and subjected to radioimmunoassay.

(C) Reverse Phase Liquid Chromatography

The basic FGF from heparin-Sepharose chromatography is pumped onto a Vydac C-4 (0.46×25 cm) reverse phase column using a 0.1% trifluoroacetic acid (TFA)/acetonitrile solvent system and eluted at 0.6 ml/min. with a 90 min.

gradient of 23% to 35% acetonitrile. Fractions of 3 ml are collected at room temperature and subjected to radioimmunoassay.

In the above mentioned Radioimmunoassays (RIA) for basic FGF, antibodies are generated against a synthetic analog of the amino terminal sequence of basic FGF, [Tyr sup 10 ]bFGF(1–10) which is conjugated to bovine serum albumin, and subsequently used to develop the radioimmunoassay for basic FGF, as described in A. Baird et al. Regulatory Peptides 10, 309–317 (1985). Because it is not possible to quantitate unmodified cysteine by amino acid analysis, cysteine residues are modified either by reduction and alkylation with [sup 14 C] iodoacetamide (New England Nuclear) or oxidization with performic acid. The bFGF in 0.1% TFA/acetonitrile is dried in a 1.5 ml polypropylene microfuge tube in a Speed Vac vacuum centrifuge (Savant, Inc.) just prior to modification.

The reduction and alkylation of cysteine residues is performed in order to radioactively label cysteine residues, making it possible to determine which fragments of subsequent cleavage reactions contain cysteine residues. The dried bFGF is dissolved in 0.1 ml deoxygenated 0.5M Tris-HCl pH 7.7, 10 mM EDTA, 6M guanidine-HCl. Dithiothreitol is added to a final concentration of 5–10 mM, and the reduction is allowed to proceed at 37 degree(s) C. for 30 min. A 0.5-fold molar excess of [sup 14C]i odoacetamide (24 mCi/mmole) over total sulfhydryl groups is added, and the incubation continued at 37 degree(s) C. for 60 min. in the dark. The alkylation is terminated by addition of a large excess of dithiothreitolover iodoacetamide, and the alkylated bFGF purified by reverse phase-high performance liquid chromatography.

Performic acid oxidation of cysteine converts cysteine to cysteic acid, and the cysteic acid content of the protein is measurable by amino acid analysis. Performic acid is generated by incubating 9 ml distilled formic acid with 1 ml 30% $H_2O_2$ at room temperature in a tightly capped tube for 1 hour. 0.25 ml of this solution is employed to dissolve the dried bFGF (5–15 nmoles), and the oxidation permitted to continue at 0 degree(s) C. for 2.5 hours. Four lyophilizations from distilled water are employed to remove reaction by-products.

Basic FGFs (with cysteines modified by each method described above) are proteolytically and chemically digested to obtain fragments for further analysis, including sequence analysis. Prior to any digestion, the bFGF is dried in a polypropylene microfuge tube in a Speed Vac vacuum centrifuge from volatile RP-HPLC solvents.

In order to obtain multiple, overlapping bFGF fragments, three types of proteolytic digestions of bFGFs, with cysteines modified by each method described above, are performed as follows. The dried bFGF (1–5 nmoles) is dissolved in 0.01 ml 0.5M Tris-HCl pH 7.7, 10 mM EDTA, 6M guanidine-HCl and then diluted to 1 ml with 1% $NH_4HCO_3$. Submaxillaris protease or chymotrypsin is added in a 1/50 (w/w) ratio while digestions with *Staphylococcus aureus* V8 employed a 1:35 (mol:mol) ratio of enzyme to substrate. Submaxillaris protease cleaves at the C-terminus of arginine; *Staphylococcus aureus* V8 cleaves at the C-terminus of glutamic acid; and chymotrypsin cleaves at the C-terminus of several amino acid residues having bulky aromatic or hydrophobic groups. Incubations are allowed to proceed overnight at 37 degree(s) C. Digestion with cyanogen bromide, which cleaves proteins at the C-terminus of Met, are performed on bFGFs, with cysteines modified by each method described above, as follows. The dried, alkylated bFGF (5–6 nmoles) is dissolved with 0.05 ml 70% formic acid and reduced in a solution of 2.9MN-methylmercaptoacetamide in 7% formic acid (R. Heighten et al. Methods in Enzymol. (eds. Hirs., C. & Timasheff, S.) 91: Academic Press, N.Y., pp.549–559 (1983)) for 24 hours at 37 degree(s) C. The alkylated, reduced bFGF is purified by RP-HPLC, dried in a Speed Vac vacuum centrifuge and redissolved in 0.1 ml deoxygenated 70% formic acid. A 100-fold excess of cyanogen bromide is added and the incubation continued at room temperature in the dark overnight.

Reverse phase-high performance liquid chromatography purifications of modified bFGFs and their digestion fragments are accomplished using a Brownlee RP-300 reverse phase column (0.46×25 cm) and a 0.1%TFA/acetonitrile or a 0.1% heptafluorobutyric acid (HFBA)/acetonitrile solvent system. PhNCS-(sup 14 C)-carboxyamidomethylcysteine is identified during sequence analysis by liquid scintillation counting of the residues from the sequencer. The identification of cysteic acid in a given cycle is accomplished by comparison of the amino acid composition of the peptide and the remainder of its sequence as determined by Edman degradation. Carboxypeptidase Y is obtained from Pierce and utilized according to the manufacturer's recommendations. Carboxyl terminal analysis via tritium incorporation is accomplished as previously described (H. Matsuo et al. Protein Sequence Determination (ed., Needleman, S. B.) Springer-Verlag, N.Y., pp. 104–113 (1979)).

EXAMPLE 5

Synthesis of a Mammalian bFGF Gene

Synthesis of a bFGF-encoding DNA chain is accomplished by synthesizing oligonucleotides on an Applied B10 Systems automatic synthesizer with overlapping complementary sequences.

The overlapping oligonucleotides are fused to form a double-stranded DNA chain, gaps are filled in with DNA polymerase and with T4 ligase. Immediately 5' of the FGF-encoding sequence in the sense strand is provided an ATG start signal, which results in an extraneous methionine being added to the N-terminus of the expressed polypeptide. Immediately 3' of the bFGF-encoding sequence is a stop signal. At the 5' end is a Eco RI overhang and at the 3' end is a Sal I overhang, whereby the synthetic DNA strand is directly insertable in the Eco RI and Sal I site of the plasmid pUC8, described by Vieira er al. Gene 14: 259–268 (1982). The DNA strand is annealed into the pUC8 plasmid where it is under the control of the betagalactosidase promoter with the ATG start signal and the Shine Delgarno sequence retained in their natural orientation and association with the promoter.

The recombinant vector, designated bFGF, is transformed into the DH-1 strain of *E. coli* by the calcium chloride procedure, CSH, supra. The transformed *E. coli* is cultured in L broth, and ampicillan- resistant strains are selected. Because the DNA chain was inserted into the plasmid in an orientation which could be expected to lead to expression of protein product of the DNA chain, the ampicillan-resistant colonies are screened for reactivity with antiserum raised against bFGF extracted from the pituitary. These colonies are screened by the immunological method of Healfman et al., Proc. Natl. Acad. Sci. USA 80: 31–35 (1983), and colonies reacting positively with bFGF antibody are further characterized. The cells separated from their culture media are lysed, and their supernatant obtained. Supernatant from transformed cells is determined by RIA to be reactive with antibody raised against bFGF. 100 ml. of cell supernatant is obtained, and bFGF is purified therefrom using heparin-Sepharose as described above. Approximately 0.01 mg of bFGF, purified to upwards of 98% by weight of total protein, is produced. The biological activity of the synthetic bFGF, which contains the extraneous N-terminal methionine residue, is tested for biological activity by the ability of the synthetic bFGF to stimulate the proliferation of adult bovine aortic arch endothelial cells in culture, as described in J.Cell Biol. 97: 1677–1685 (1983). Briefly, cells (at passage 3–10) are seeded at a density of 2×10 sup 3 cells/dish on plastic tissue culture dishes and exposed to Dulbecco's modified Eagle's medium (DMEM) supplemented with 10% calf serum. Test samples, at a dilution ranging from 10 sup −1 to 10 sup −3, are added on day 0 and day 2 to the dishes. On day 4, triplicate dishes are trypsinized and counted in a Coulter counter. Background levels are ordinarily 10 sup 5 cells/dish, while those exposed to optimal concentrations of the growth factor can contain as much as 5 to 8×10 sup 5 cells. For a potency assay, a log response curve was established. For this purpose, 10 microliter-aliquots of a dilution (ranging from 10 sup −1 to sup −5) of the original solution made in 0.5%BSA/DMEM were added in triplicate.

The biological (mitogenic) activity of synthetic bFGF is substantially identical to natural, purified bFGF from bovine pituitary cells. The superfluous N-terminal residue is removable by partial chemical digestion with cyanogen bromide or phenyl isothiocyanate followed by treatment with a strong anhydrous acid, such as trifluoroacetic acid.

While the principles of the invention have been made clear in illustrative embodiments, there will be immediately obvious to those skilled in the art many modifications of structure, arrangement, proportions, the elements, materials, and components used in the practice of the invention, and otherwise, which are particularly adapted to specific environments and operative requirements without departing from those principles. The appended claims are intended to cover and embrace any and all such modifications, with the limits only of the true spirit and scope of the invention.

We claim:

1. An apparatus for treatment of body tissue, comprising:

a treatment apparatus configured to be inserted into a patient, the treatment apparatus including a distal portion, a distal end, a proximal portion and an axis;

a non-rotating ultrasound transducer positioned at the distal portion of the treatment apparatus, the ultrasound transducer including a distal ultrasound energy delivery surface and a proximal ultrasound energy delivery surface; and an ultrasound energy attenuator member positioned adjacent to the proximal ultrasound energy delivery surface and made of a material to at least partially attenuate ultrasound energy from the proximal ultrasound energy delivery surface.

2. The apparatus of claim 1, wherein the ultrasound transducer is positioned to transmit ultrasound signals substantially axially aligned with the axis of the treatment apparatus to the body tissue, the ultrasound transducer further receiving return signals from the body tissue to be treated.

3. The apparatus of claim 2, further comprising:

a signal interface coupled to the ultrasound transducer, the signal interface receiving at least a portion of the return signals from the cardio vascular tissue; and a signal processor coupled to the signal interface, the signal processor providing a real time determination of at least one surface of body tissue relative to one or more positions of the distal end of the treatment apparatus.

4. The apparatus of claim 1, wherein the ultrasound energy attenuator member attenuates ultrasound energy from the proximal ultrasound energy delivery surface in an amount of 10–30 dB.

5. The apparatus of claim 1, wherein the ultrasound energy attenuator member attenuates ultrasound energy from the proximal ultrasound energy delivery surface in an amount of 15–25 dB.

6. The apparatus of claim 1, wherein the ultrasound energy attenuator member attenuates ultrasound energy from the proximal ultrasound energy delivery surface in an amount of 20 dB.

7. The apparatus of claim 1, wherein the transducer operates in a frequency range of 1–40 MHz.

8. The apparatus of claim 1, wherein the transducer operates in a frequency range of 5–30 MHz.

9. The apparatus of claim 1, wherein the transducer operates in a frequency range of 10–20 MHz.

10. The apparatus of claim 1, wherein the ultrasound energy attenuator member attenuates ultrasound energy in an amount of at least 40 dB in a distance of 3 mm or less.

11. The apparatus of claim 1, wherein the ultrasound energy attenuator member attenuates ultrasound energy in an amount of at least 30 dB in a distance of 3 mm or less.

12. The apparatus of claim 1, wherein the ultrasound energy attenuator member attenuates ultrasound energy in an amount of at least 20 dB in a distance of 3 mm or less.

13. The apparatus of claim 1, wherein the ultrasound energy attenuator member attenuates ultrasound energy in an amount of at least 40 dB in a distance of 2 mm or less.

14. The apparatus of claim 1, wherein the ultrasound energy attenuator member attenuates ultrasound energy in an amount of at least 30 dB in a distance of 2 mm or less.

15. The apparatus of claim 1, wherein the ultrasound energy attenuator member attenuates ultrasound energy in an amount of at least 20 dB in a distance of 2 mm or less.

16. The apparatus of claim 1, wherein the ultrasound energy attenuator member has a distal end positioned adjacent to the proximal ultrasound energy delivery surface and an opposing proximal end, wherein a diameter of the attenuator member distal end is greater than a diameter of the attenuator member proximal end.

17. The apparatus of claim 1, wherein the ultrasound energy attenuator member has a tapered geometric configuration.

18. The apparatus of claim 1, wherein the ultrasound energy attenuator member includes a plurality of microspheres.

19. The apparatus of claim 1, wherein the plurality of microspheres expand upon a receipt of ultrasound energy.

20. The apparatus of claim 1, further comprising:

an electrode positioned at the distal end of the treatment apparatus.

21. The apparatus of claim 20, wherein the electrode has a tissue interface surface of sufficient size to provide a detection of an ECG signal.

22. The apparatus of claim 20, further comprising:

a multiplexer coupled to the electrode and the ultrasound transducer.

23. The apparatus of claim 22, wherein the multiplexer provides a multiplexing of a signals of the electrode and the ultrasound transducer.

24. The apparatus of claim 1, further comprising:

an energy delivery device retractably positioned in a treatment apparatus lumen.

25. The apparatus of claim 24, wherein the energy delivery device is an optical fiber.

26. The apparatus of claim 24, further comprising:

an energy delivery device retraction member coupled to the energy delivery device.

27. The apparatus of claim 26, wherein the energy delivery device retraction member is coupled to the treatment apparatus.

28. The apparatus of claim 24, wherein the energy delivery device is sufficiently retractable within the treatment apparatus lumen to permit transmission of ultrasound signals in a lateral angle of 30° or less relative to the axis of the treatment apparatus to the body tissue, the ultrasound transducer further receiving return signals from the body tissue to be treated.

29. The apparatus of claim 24, wherein the energy delivery device is sufficiently retractable within the treatment apparatus lumen to permit transmission of ultrasound signals in a lateral angle of 20° or less relative to the axis of the treatment apparatus to the body tissue, the ultrasound transducer further receiving return signals from the body tissue to be treated.

30. The apparatus of claim 24, wherein the energy delivery device is sufficiently retractable within the treatment apparatus lumen to permit transmission of ultrasound signals in a lateral angle of 10° or less relative to the axis of the treatment apparatus to the body tissue, the ultrasound transducer further receiving return signals from the body tissue to be treated.

31. The apparatus of claim 24, wherein the energy delivery device is sufficiently retractable within the treatment apparatus lumen to permit transmission of ultrasound signals substantially axially aligned with the axis of the treatment apparatus to the body tissue, the ultrasound transducer further receiving return signals from the body tissue to be treated.

32. The apparatus of claim 1, wherein the treatment apparatus includes an agent delivery lumen.

33. The apparatus of claim 32, wherein the agent is an angiogenesis stimulation agent.

34. The apparatus of claim 1, further comprising:

a catheter having at least one lumen for guiding the treatment apparatus.

35. The apparatus of claim 34, wherein the catheter is sized and configured for insertion through the vasculature of the patient.

36. The apparatus of claim 1, further comprising:

an MIS apparatus having at least one lumen for guiding the treatment apparatus.

37. The apparatus of claim 1, further comprising:

a surgical handpiece having at least one lumen for insertion of the treatment apparatus therethrough.

38. The apparatus of claim 1, wherein the treatment apparatus includes a laser delivery device.

39. The apparatus of claim 38, wherein the laser delivery device includes an optical fiber.

40. The apparatus of claim 38, further comprising:

a laser energy source coupled to the laser delivery device.

41. The apparatus of claim 40, wherein the laser energy source is a holmium laser.

42. The apparatus of claim 40, wherein the laser energy source is an eximer laser.

43. The apparatus of claim 40, wherein the laser energy source is a $CO_2$ laser.

44. The apparatus of claim 1, wherein the treatment apparatus is a mechanical cutting apparatus suitable for performing myocardial revascularization.

45. The apparatus of claim 1, wherein the body tissue is a cardiovascular tissue.

46. The apparatus of claim 1, wherein the body tissue is a myocardium tissue.

47. The apparatus of claim 1, wherein the patient is a human patient.

48. An apparatus for treatment of body tissue, comprising:

a treatment apparatus configured to be inserted into a patient, the treatment apparatus including a distal portion, a distal end, a proximal portion and an axis;

an ultrasound transducer positioned at the distal portion of the treatment apparatus, the ultrasound transducer including a distal ultrasound energy delivery surface and a proximal ultrasound energy delivery surface; and an electrode positioned adjacent to the ultrasound transducer at the treatment apparatus distal end.

49. The apparatus of claim 48, wherein the electrode has a tissue interface surface of sufficient size to provide a detection of an ECG signal.

50. The apparatus of claim 48, further comprising:

a multiplexer coupled to the electrode and the ultrasound transducer.

51. The apparatus of claim 50, wherein the multiplexer provides a multiplexing of a signals of the electrode and the ultrasound transducer.

52. The apparatus of claim 51, further comprising:

an energy delivery device retractably positioned in a treatment apparatus lumen.

53. The apparatus of claim 52, wherein the energy delivery device is an optical fiber.

54. The apparatus of claim 52, further comprising:

an energy delivery device retraction member coupled to the energy delivery device.

55. The apparatus of claim 54, wherein the energy delivery device retraction member is coupled to the treatment apparatus.

56. The apparatus of claim 54, wherein the energy delivery device is sufficiently retractable within the treatment apparatus lumen to permit transmission of ultrasound signals in a lateral angle of 30° or less relative to the axis of the treatment apparatus to the body tissue, the ultrasound transducer further receiving return signals from the body tissue to be treated.

57. The apparatus of claim 54, wherein the energy delivery device is sufficiently retractable within the treatment apparatus lumen to permit transmission of ultrasound signals in a lateral angle of 20° or less relative to the axis of the treatment apparatus to the body tissue, the ultrasound transducer further receiving return signals from the body tissue to be treated.

58. The apparatus of claim 54, wherein the energy delivery device is sufficiently retractable within the treatment apparatus lumen to permit transmission of ultrasound signals in a lateral angle of 10° or less relative to the axis of the treatment apparatus to the body tissue, the ultrasound transducer further receiving return signals from the body tissue to be treated.

59. The apparatus of claim 54, wherein the energy delivery device is sufficiently retractable within the treatment apparatus lumen to permit transmission of ultrasound signals substantially axially aligned with the axis of the treatment apparatus to the body tissue, the ultrasound transducer further receiving return signals from the body tissue to be treated.

60. The apparatus of claim 48, wherein the treatment apparatus includes an agent delivery lumen.

61. The apparatus of claim 48, wherein the agent is an angiogenesis stimulation agent.

62. The apparatus of claim 48, further comprising:

an ultrasound energy attenuator member positioned adjacent to the proximal ultrasound energy delivery surface and made of a material to at least partially attenuate ultrasound energy from the proximal ultrasound energy delivery surface.

63. The apparatus of claim 62, wherein the ultrasound energy attenuator member attenuates ultrasound energy from the proximal ultrasound energy delivery surface in an amount of 10–30 dB.

64. The apparatus of claim 62, wherein the ultrasound energy attenuator member attenuates ultrasound energy from the proximal ultrasound energy delivery surface in an amount of 15–25 dB.

65. The apparatus of claim 62, wherein the ultrasound energy attenuator member attenuates ultrasound energy from the proximal ultrasound energy delivery surface in an amount of 20 dB.

66. The apparatus of claim 62, wherein the transducer operates in a frequency range of 1–40 MHz.

67. The apparatus of claim 62, wherein the transducer operates in a frequency range of 5–30 MHz.

68. The apparatus of claim 62, wherein the transducer operates in a frequency range of 10–20 MHz.

69. The apparatus of claim 62, wherein the ultrasound energy attenuator member attenuates ultrasound energy in an amount of at least 40 dB in a distance of 3 mm or less.

70. The apparatus of claim 62, wherein the ultrasound energy attenuator member attenuates ultrasound energy in an amount of at least 30 dB in a distance of 3 mm or less.

71. The apparatus of claim 62, wherein the ultrasound energy attenuator member attenuates ultrasound energy in an amount of at least 20 dB in a distance of 3 mm or less.

72. The apparatus of claim 62, wherein the ultrasound energy attenuator member attenuates ultrasound energy in an amount of at least 40 dB in a distance of 2 mm or less.

73. The apparatus of claim 62, wherein the ultrasound energy attenuator member attenuates ultrasound energy in an amount of at least 30 dB in a distance of 2 mm or less.

74. The apparatus of claim 62, wherein the ultrasound energy attenuator member attenuates ultrasound energy in an amount of at least 20 dB in a distance of 2 mm or less.

75. The apparatus of claim 62, wherein the ultrasound energy attenuator member has a distal end positioned adjacent to the proximal ultrasound energy delivery surface and an opposing proximal end, wherein a diameter of the attenuator member distal end is greater than a diameter of the attenuator member proximal end.

76. The apparatus of claim 62, wherein the ultrasound energy attenuator member has a tapered geometric configuration.

77. The apparatus of claim 62, wherein the ultrasound energy attenuator member includes a plurality of microspheres.

78. The apparatus of claim 60, wherein the plurality of microspheres expand upon a receipt of ultrasound energy.

79. The apparatus of claim 48, wherein the body tissue is a cardiovascular tissue.

80. The apparatus of claim 48, wherein the body tissue is a myocardium tissue.

81. The apparatus of claim 48, wherein the patient is a human patient.

82. An apparatus for treatment of body tissue, comprising:

a treatment apparatus configured to be inserted into a patient, the treatment apparatus including a distal portion, a distal end, a proximal portion, a treatment apparatus lumen and an axis;

an ultrasound transducer to transmit ultrasonic signals to body tissue positioned at the distal portion of the treatment apparatus, the ultrasound transducer including a distal ultrasound energy delivery surface and a proximal ultrasound energy delivery surface; and a retractable energy delivery device retractably positionable in the treatment apparatus lumen.

83. The apparatus of claim 82, wherein the energy delivery device is an optical fiber.

84. The apparatus of claim 82, further comprising:

an energy delivery device retraction member coupled to the energy delivery device.

85. The apparatus of claim 84, wherein the energy delivery device retraction member is coupled to the treatment apparatus.

86. The apparatus of claim 84, wherein the energy delivery device is sufficiently retractable within the treatment apparatus lumen to permit transmission of ultrasound signals in a lateral angle of 30° or less relative to the axis of the treatment apparatus to the body tissue, the ultrasound transducer further receiving return signals from the body tissue to be treated.

87. The apparatus of claim 84, wherein the energy delivery device is sufficiently retractable within the treatment apparatus lumen to permit transmission of ultrasound signals in a lateral angle of 20° or less relative to the axis of the treatment apparatus to the body tissue, the ultrasound transducer further receiving return signals from the body tissue to be treated.

88. The apparatus of claim 84, wherein the energy delivery device is sufficiently retractable within the treatment apparatus lumen to permit transmission of ultrasound signals in a lateral angle of 10° or less relative to the axis of the treatment apparatus to the body tissue, the ultrasound transducer further receiving return signals from the body tissue to be treated.

89. The apparatus of claim 84, wherein the energy delivery device is sufficiently retractable within the treatment apparatus lumen to permit transmission of ultrasound signals substantially axially aligned with the axis of the treatment apparatus to the body tissue, the ultrasound transducer further receiving return signals from the body tissue to be treated.

90. The apparatus of claim 82, wherein the treatment apparatus includes an agent delivery lumen.

91. The apparatus of claim 90, wherein the agent is an angiogenesis stimulation agent.

92. The apparatus of claim 82, further comprising:

an electrode positioned adjacent to the ultrasound transducer at the treatment apparatus distal end.

93. The apparatus of claim 92, wherein the electrode has a tissue interface surface of sufficient size to provide a detection of an ECG signal.

94. The apparatus of claim 92, further comprising:

a multiplexer coupled to the electrode and the ultrasound transducer.

95. The apparatus of claim 94, wherein the multiplexer provides a multiplexing of a signals of the electrode and the ultrasound transducer.

96. The apparatus of claim 82, further comprising:

an ultrasound energy attenuator member positioned adjacent to the proximal ultrasound energy delivery surface and made of a material to at least partially attenuate ultrasound energy from the proximal ultrasound energy delivery surface.

97. The apparatus of claim 96, wherein the ultrasound energy attenuator member attenuates ultrasound energy from the proximal ultrasound energy delivery surface in an amount of 10–30 dB.

98. The apparatus of claim 96, wherein the ultrasound energy attenuator member attenuates ultrasound energy from the proximal ultrasound energy delivery surface in an amount of 15–25 dB.

99. The apparatus of claim 96, wherein the ultrasound energy attenuator member attenuates ultrasound energy from the proximal ultrasound energy delivery surface in an amount of 20 dB.

100. The apparatus of claim 96, wherein the transducer operates in a frequency range of 1–40 MHz.

101. The apparatus of claim 96, wherein the transducer operates in a frequency range of 5–30 MHz.

102. The apparatus of claim 96, wherein the transducer operates in a frequency range of 10–20 MHz.

103. The apparatus of claim 96, wherein the ultrasound energy attenuator member attenuates ultrasound energy in an amount of at least 40 dB in a distance of 3 mm or less.

104. The apparatus of claim 96, wherein the ultrasound energy attenuator member attenuates ultrasound energy in an amount of at least 30 dB in a distance of 3 mm or less.

105. The apparatus of claim 96, wherein the ultrasound energy attenuator member attenuates ultrasound energy in an amount of at least 20 dB in a distance of 3 mm or less.

106. The apparatus of claim 96, wherein the ultrasound energy attenuator member attenuates ultrasound energy in an amount of at least 40 dB in a distance of 2 mm or less.

107. The apparatus of claim 96, wherein the ultrasound energy attenuator member attenuates ultrasound energy in an amount of at least 30 dB in a distance of 2 mm or less.

108. The apparatus of claim 96, wherein the ultrasound energy attenuator member attenuates ultrasound energy in an amount of at least 20 dB in a distance of 2 mm or less.

109. The apparatus of claim 96, wherein the ultrasound energy attenuator member has a distal end positioned adjacent to the proximal ultrasound energy delivery surface and an opposing proximal end, wherein a diameter of the attenuator member distal end is greater than a diameter of the attenuator member proximal end.

110. The apparatus of claim 96, wherein the ultrasound energy attenuator member has a tapered geometric configuration.

111. The apparatus of claim 96, wherein the ultrasound energy attenuator member includes a plurality of microspheres.

112. The apparatus of claim 96, wherein the plurality of microspheres expand upon a receipt of ultrasound energy.

113. The apparatus of claim 82, wherein the body tissue is a cardiovascular tissue.

114. The apparatus of claim 82, wherein the body tissue is a myocardium tissue.

115. The apparatus of claim 82, wherein the patient is a human patient.

* * * * *